(12) United States Patent
Hourtash

(10) Patent No.: US 11,173,598 B2
(45) Date of Patent: Nov. 16, 2021

(54) SYSTEM AND METHODS FOR MANAGING MULTIPLE NULL-SPACE OBJECTIVES AND SLI BEHAVIORS

(71) Applicant: Intuitive Surgical Operations, Inc., Sunnyvale, CA (US)

(72) Inventor: Arjang M. Hourtash, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 95 days.

(21) Appl. No.: 16/670,825

(22) Filed: Oct. 31, 2019

(65) Prior Publication Data
US 2020/0061813 A1    Feb. 27, 2020

Related U.S. Application Data

(63) Continuation of application No. 15/967,545, filed on Apr. 30, 2018, now Pat. No. 10,513,031, which is a
(Continued)

(51) Int. Cl.
*B25J 9/16*    (2006.01)
*B25J 18/00*    (2006.01)
(Continued)

(52) U.S. Cl.
CPC ............. *B25J 9/1607* (2013.01); *A61B 34/30* (2016.02); *A61B 34/37* (2016.02); *B25J 9/1689* (2013.01);
(Continued)

(58) Field of Classification Search
CPC ...... B25J 9/1607; B25J 9/1689; B25J 18/007; A61B 34/30; A61B 34/37; A61B 34/77;
(Continued)

(56) References Cited

U.S. PATENT DOCUMENTS

| 5,430,643 A | 7/1995 | Seraji |
|---|---|---|
| 9,510,911 B2 | 12/2016 | Hourtash |

(Continued)

FOREIGN PATENT DOCUMENTS

| EP | 2332484 A2 | 6/2011 |
|---|---|---|
| JP | H04340603 A | 11/1992 |

(Continued)

OTHER PUBLICATIONS

Baerlocher, P. et al., "Task Priority Formulations for the Kinematic Control of Highly Redundant Articulated Structures," IEEE/RSJ International Conference on Intelligent Robots and Systems, 1998, vol. 1, pp. 323-329.

(Continued)

*Primary Examiner* — Jeffrey Donels
(74) *Attorney, Agent, or Firm* — Ferguson Braswell Fraser Kubasta PC

(57) ABSTRACT

A method for moving a manipulator arm. The manipulator arm includes a movable distal portion, a proximal portion coupled to a base, and joints between the distal portion and the base. The method involves calculating a first movement of the joints in accordance with a first objective. The method further involves calculating a second movement of the joints in accordance with a second objective. The first and the second movements are in a null-space of a Jacobian of the manipulator arm. The method also involves determining a combined movement of the joints by combining the first and second movements while limiting an overall magnitude of the combined movement without changing a direction of the combined movement, and/or combining the first and second movements while limiting a magnitude of the combined movement degree-of-freedom by degree-of-freedom. The method further involves driving the joints to effect the combined movement of the joints.

20 Claims, 23 Drawing Sheets

Related U.S. Application Data continuation of application No. 15/359,413, filed on Nov. 22, 2016, now Pat. No. 10,029,367, which is a continuation of application No. 14/218,832, filed on Mar. 18, 2014, now Pat. No. 9,510,911.

(60) Provisional application No. 61/800,810, filed on Mar. 15, 2013.

(51) Int. Cl.
*A61B 34/30* (2016.01)
*A61B 34/37* (2016.01)
*A61B 34/00* (2016.01)

(52) U.S. Cl.
CPC ............ *B25J 18/007* (2013.01); *A61B 34/77* (2016.02); *G05B 2219/39079* (2013.01); *G05B 2219/40327* (2013.01); *G05B 2219/41405* (2013.01)

(58) Field of Classification Search
CPC ........... G05B 2219/39079; G05B 2219/40327; G05B 2219/41405
See application file for complete search history.

(56) References Cited

U.S. PATENT DOCUMENTS

| | | | |
|---|---|---|---|
| 10,029,367 B2 | 7/2018 | Hourtash et al. | |
| 2002/0120363 A1 | 8/2002 | Salisbury et al. | |
| 2007/0013336 A1* | 1/2007 | Nowlin .................. | A61B 34/30 318/568.21 |
| 2007/0151389 A1* | 7/2007 | Prisco .................... | A61B 34/70 74/490.05 |
| 2008/0221592 A1* | 9/2008 | Kawai .................. | A61B 1/0055 606/130 |
| 2012/0123441 A1* | 5/2012 | Au ........................ | A61B 34/30 606/130 |
| 2014/0195054 A1* | 7/2014 | Kamiya .................. | B25J 13/06 700/263 |
| 2014/0276953 A1* | 9/2014 | Swarup .................. | B25J 18/007 606/130 |
| 2014/0276954 A1* | 9/2014 | Hourtash ............... | B25J 9/1666 606/130 |
| 2014/0277741 A1* | 9/2014 | Kwon .................... | B25J 9/1689 700/263 |
| 2014/0358161 A1* | 12/2014 | Hourtash ............... | A61B 34/37 606/130 |
| 2018/0243906 A1 | 8/2018 | Hourtash | |

FOREIGN PATENT DOCUMENTS

| | | |
|---|---|---|
| WO | WO-2007076119 A2 | 7/2007 |
| WO | WO-2013038544 A1 | 3/2013 |
| WO | WO-2013078529 A1 | 6/2013 |

OTHER PUBLICATIONS

Funda J., et al., "Constrained Cartesian Motion Control for Teleoperated Surgical Robots," IEEE Transactions on Robotics and Automation, IEEE, Jun. 1996, vol. 12 (3), pp. 453-465.

International Search Report and Written Opinion for Application No. PCT/US14/31055, dated Jul. 29, 2014, 17 pages (ISRG03790/PCT).

Jamshidi et al., "Robotics and Manufacturing—Recent Trends in Research, Education and Applications," Proceedings of the Second International Symposium of Robotics and Manufacturing: Research, Education, and Applications, ASME Press, Nov. 16-18, 1988, 17 pages.

Maciejewski A.A., et al., "Obstacle Avoidance for Kinematically Redundant Manipulators in Dynamically Varying Environments," International Journal of Robotics Research, 1985, vol. 4 (3), pp. 109-116.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

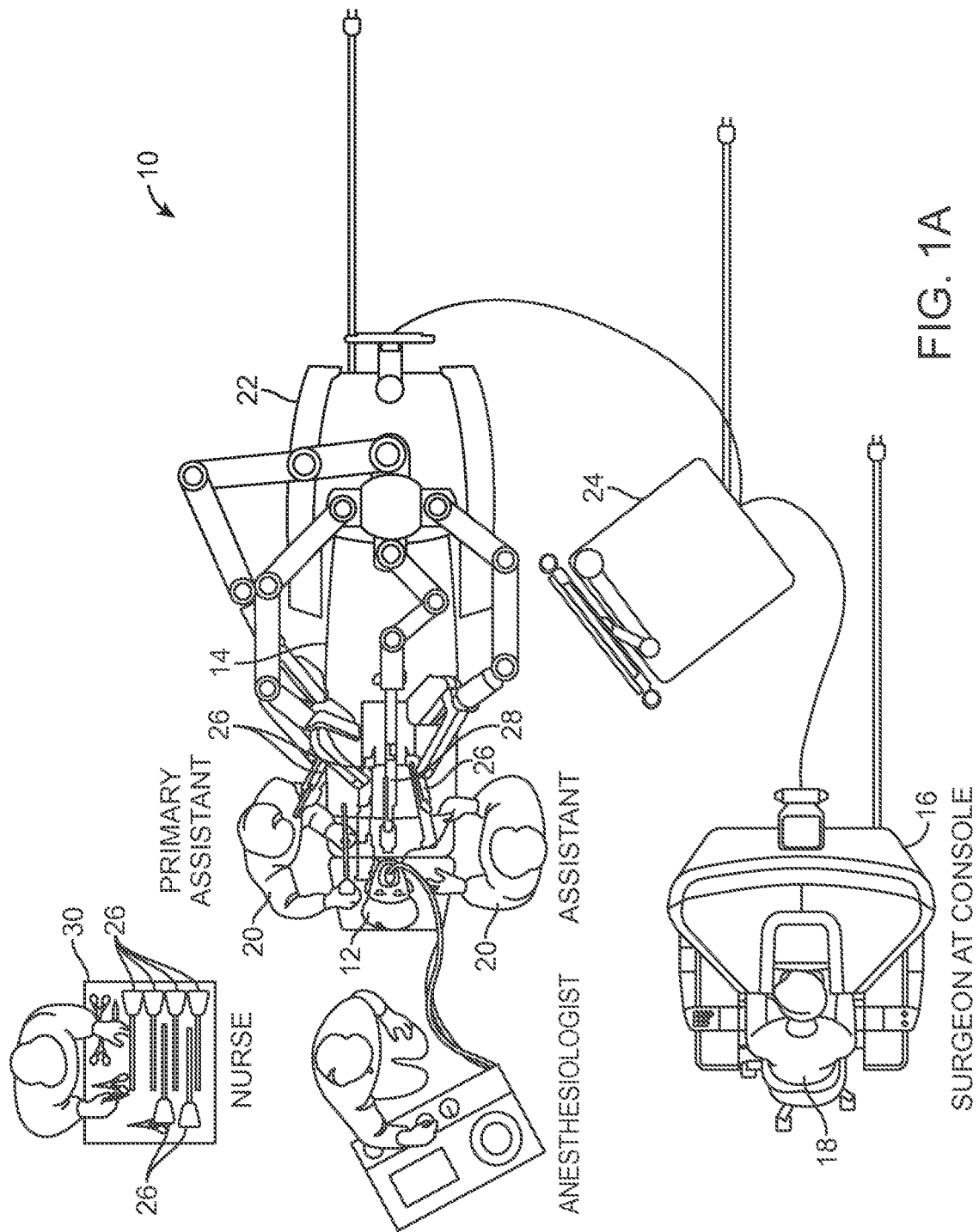

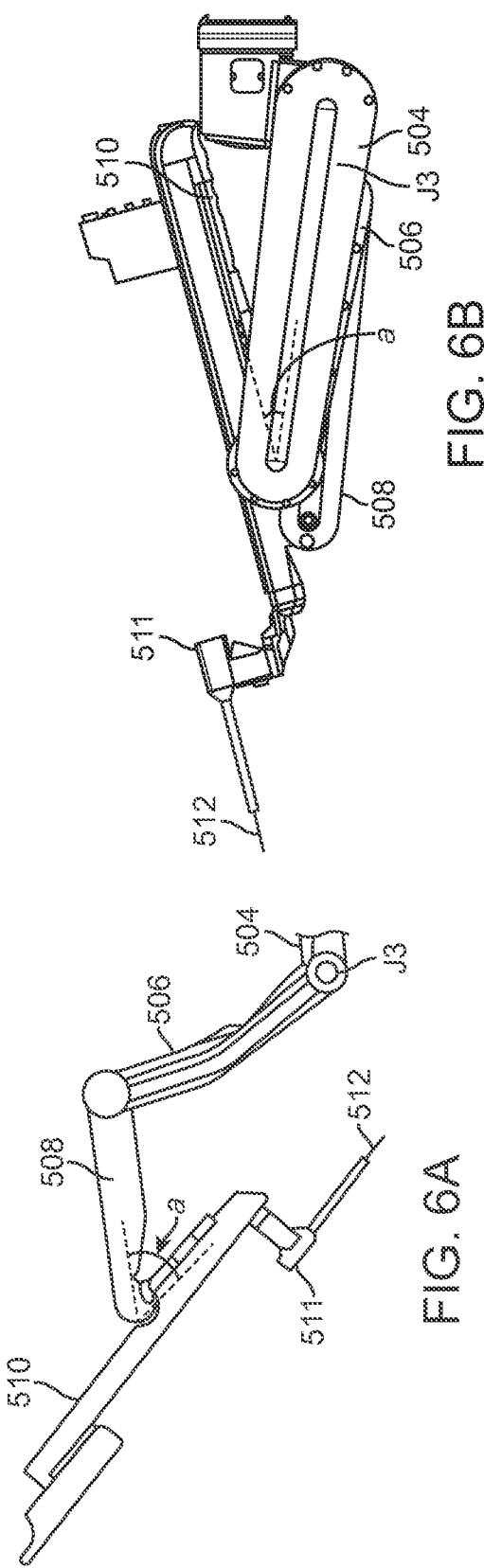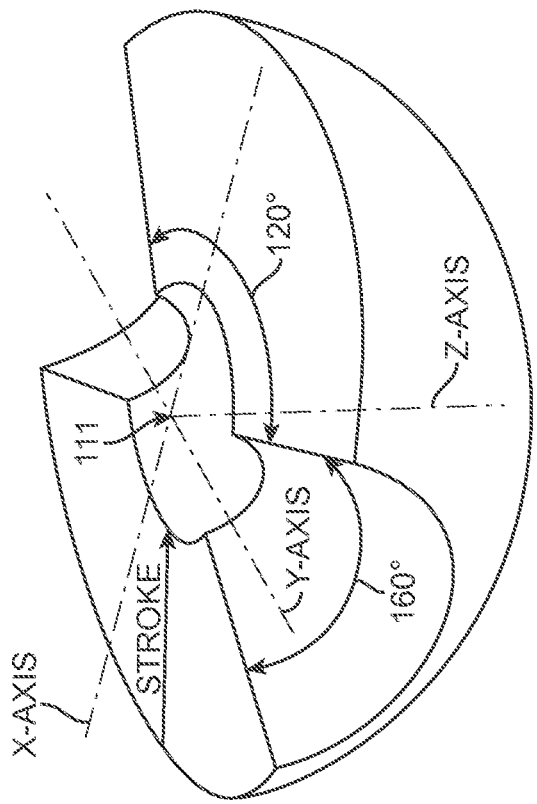
FIG. 6A
FIG. 6B
FIG. 6C

SYSTEM AND METHODS FOR MANAGING MULTIPLE NULL-SPACE OBJECTIVES AND SLI BEHAVIORS

CROSS-REFERENCES TO RELATED APPLICATIONS

This application is a continuation of and claims the benefit of priority under 35 U.S.C § 120 to U.S. patent application Ser. No. 15/967,545, filed on Apr. 30, 2018, which is a continuation of and claims the benefit of priority under 35 U.S.C § 120 to U.S. patent application Ser. No. 15/359,413, filed Nov. 22, 2016, which is a continuation of and claims the benefit of priority under 35 U.S.C § 120 to U.S. patent application Ser. No. 14/218,832, filed on Mar. 18, 2014, which is a Non-Provisional of and claims the benefit of priority from U.S. Provisional Patent Application No. 61/800,810 filed on Mar. 15, 2013 and entitled "Systems and Methods for Managing Multiple Null-Space Objectives and SLI Behaviors", the full disclosure of each of which is incorporation herein by reference.

The present application is generally related to the following commonly-owned applications: U.S. application Ser. No. 12/494,695 filed Jun. 30, 2009, entitled "Control of Medical Robotic System Manipulator About Kinematic Singularities;" U.S. application Ser. No. 12/406,004 filed Mar. 17, 2009, entitled "Master Controller Having Redundant Degrees of Freedom and Added Forces to Create Internal Motion;" U.S. application Ser. No. 11/133,423 filed May 19, 2005 (U.S. Pat. No. 8,004,229), entitled "Software Center and Highly Configurable Robotic Systems for Surgery and Other Uses;" U.S. application Ser. No. 10/957,077 filed Sep. 30, 2004 (U.S. Pat. No. 7,594,912), entitled "Offset Remote Center Manipulator For Robotic Surgery;" and U.S. application Ser. No. 09/398,507 filed Sep. 17, 1999 (U.S. Pat. No. 6,714,839), entitled "Master Having Redundant Degrees of Freedom;" U.S. application Ser. No. 12/494,695 filed Jun. 30, 2009, entitled "Control of Medical Robotic System Manipulators About Kinematic Singularities;" U.S. Provisional Application No. 61/654,755 filed Jun. 1, 2012, entitled "Manipulator Arm-to-Patient Collision Avoidance Using a Null-Space;" U.S. Provisional Application No. 61/654,773 filed Jun. 1, 2012, entitled "System and Methods for Avoiding Collisions Between Manipulator Arms Using a Null-Space," and the following U.S. Provisional Application Nos. 61/800,381; 61/800,924 and 61/799,920 filed Mar. 15, 2013, the disclosures of which are incorporated herein by reference in their entireties.

BACKGROUND OF THE INVENTION

The present invention generally provides improved surgical and/or robotic devices, systems, and methods.

Minimally invasive medical techniques are aimed at reducing the amount of tissue which is damaged during diagnostic or surgical procedures, thereby reducing patient recovery time, discomfort, and deleterious side effects. Millions of "open" or traditional surgeries are performed each year in the United States; many of these surgeries can potentially be performed in a minimally invasive manner. However, only a relatively small number of surgeries currently use minimally invasive techniques due to limitations in surgical instruments, and techniques, and the additional surgical training required to master them.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn controls the motion of robotic instruments. The robotic surgical instruments can be inserted through small, minimally invasive surgical apertures to treat tissues at surgical sites within the patient, often avoiding the trauma associated with accessing for open surgery. These robotic systems can move the working ends of the surgical instruments with sufficient dexterity to perform quite intricate surgical tasks, such as by pivoting shafts of the instruments at the minimally invasive aperture, sliding of the shaft axially through the aperture, rotating of the shaft within the aperture, and/or the like.

The servomechanism used for telesurgery will often accept input from two master controllers (one for each of the surgeon's hands) and may include two or more robotic arms or manipulators. Mapping of the hand movements to the image of the robotic instruments displayed by the image capture device can help provide the surgeon with accurate control over the instruments associated with each hand. In many surgical robotic systems, one or more additional robotic manipulator arms are included for moving an endoscope or other image capture device, additional surgical instruments, or the like.

A variety of structural arrangements can be used to support the surgical instrument at the surgical site during robotic surgery. The driven linkage or "slave" is often called a robotic surgical manipulator, and example as a robotic surgical manipulator during minimally invasive robotic surgery are described in U.S. Pat. Nos. 6,758,843; 6,246,200; and 5,800,423, the full disclosures of which are incorporated herein by reference. These linkages often make use of a parallelogram arrangement to hold an instrument having a shaft. Such a manipulator structure can constrain movement of the instrument so that the instrument shaft pivots about a remote center of spherical rotation positioned in space along the length of the rigid shaft. By aligning this center of rotation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 6,702,805; 6,676,669; 5,855, 583; 5,808,665; 5,445,166; and 5,184,601, the full disclosures of which are incorporated herein by reference.

While the new robotic surgical systems and devices have proven highly effective and advantageous, still further improvements would be desirable. For example, a manipulator arm may include additional redundant joints to provide increased movements or configurations under certain conditions. When moving surgical instruments within a minimally invasive surgical site, however, these joints may exhibit a significant amount of movement outside the patient, often more movement than needed or expected, particularly when pivoting instruments about minimally invasive apertures through large angular ranges. Alternative manipulator structures have been proposed which employ software control over joints of a highly configurable kinematic manipulator to restrain pivotal motion at the insertion site while inhibiting inadvertent manipulator/manipulator contact outside the patient (or the like). These highly configurable "software center" surgical manipulator systems may provide significant advantages, but may also present challenges. In particular, the mechanically constrained remote-center linkages may offer safety advantages in some conditions. Additionally, the wide range of configurations of the numerous joints often included in these manipulators may result in the manipulators being difficult to manually set-up in a configuration that is desirable for a particular procedure. As the range of surgeries being performed using telesurgical systems continues to expand, there is an increasing demand for expanding the available configurations and the range of motion of the instruments within the patient. Unfortunately, both of these changes can increase the challenges associated with the motion of the manipulators outside the body, and further increase the importance of avoiding unnecessary movement of the manipulators arm and undesirable configurations and movements.

For these and other reasons, it would be advantageous to provide improved devices, systems, and methods for surgery, robotic surgery, and other robotic applications. It would be particularly beneficial if these improved technologies provided the ability to limit the amount of movement of the manipulator arm and/or provided one or more beneficial movements during certain tasks. Additionally, it would be desirable to provide such improvements while increasing the range of motion of the instruments for at least some tasks and without significantly increasing the size, mechanical complexity, or costs of these systems, and while maintaining or improving their dexterity.

BRIEF SUMMARY OF THE INVENTION

In general, in one aspect, one or more embodiments relate to a method for moving a manipulator arm, the manipulator arm including a movable distal portion, a proximal portion coupled to a base, and a plurality of joints between the distal portion and the base, the plurality of joints having sufficient degrees of freedom to allow a range of differing joint states of the plurality of joints for a given state of the distal portion, the method comprising: calculating a first movement of the plurality of joints in accordance with a first objective of a plurality of objectives, the plurality of objectives being for motions in a null-space of a Jacobian of the manipulator arm, wherein the first movement is in the null-space; calculating a second movement of the plurality of joints in accordance with a second objective of the plurality of objectives, wherein the second movement is in the null-space; determining a combined movement of the plurality of joints by using a combining behavior selected from the group consisting of: combining the first and second movements while limiting an overall magnitude of the combined movement without changing a direction of the combined movement, and combining the first and second movements while limiting a magnitude of the combined movement degree-of-freedom by degree-of-freedom; and driving the plurality of joints to effect the combined movement of the plurality of joints.

In general, in one aspect, one or more embodiments relate to a system, the system comprising: a manipulator arm including a movable distal portion, a proximal portion coupled to a base, and a plurality of joints between the distal portion and the base, the plurality of joints having sufficient degrees of freedom to allow a range of differing joint states of the plurality of joints for a given state of the distal portion; a processor coupled to the manipulator arm, the processor being configured to perform operations including: calculating a first movement of the plurality of joints in accordance with a first objective of a plurality of objectives, the plurality of objectives being for motions in a null-space of a Jacobian of the manipulator arm, wherein the first movement is in the null-space; calculating a second movement of the plurality of joints in accordance with a second objective of the plurality of objectives, wherein the second movement is in the null-space; determining a combined movement of the plurality of joints by using a combining behavior selected from the group consisting of: combining the first and second movements while limiting an overall magnitude of the combined movement without changing a direction of the combined movement, and combining the first and second movements while limiting a magnitude of the combined movement degree-of-freedom by degree-of-freedom; and driving the plurality of joints to effect the combined movement of the plurality of joints.

In general, in one aspect, one or more embodiments relate to a non-transitory computer readable medium including computer readable program code for causing a computer system to perform operations for moving a manipulator arm, the manipulator arm including a movable distal portion, a proximal portion coupled to a base, and a plurality of joints between the distal portion and the base, the plurality of joints having sufficient degrees of freedom to allow a range of differing joint states of the plurality of joints for a given state of the distal portion, the operations comprising: calculating a first movement of the plurality of joints in accordance with a first objective of a plurality of objectives, the plurality of objectives being for motions in a null-space of a Jacobian of the manipulator arm, wherein the first movement is in the null-space; calculating a second movement of the plurality of joints in accordance with a second objective of the plurality of objectives, wherein the second movement is in the null-space; determining a combined movement of the plurality of joints by: combining the first and second movements while limiting an overall magnitude of the combined movement without changing a direction of the combined movement, or combining the first and second movements while limiting a magnitude of the combined movement degree-of-freedom by degree-of-freedom; and driving the plurality of joints to effect the combined movement of the plurality of joints.

A further understanding of the nature and advantages of the present invention will become apparent by reference to the remaining portions of the specification and drawings.

BRIEF DESCRIPTION OF THE DRAWINGS

FIG. 1A is an overhead view of a robotic surgical system in accordance with embodiments of the present invention, the robotic surgical system having a surgical station with a plurality of robotic manipulators for robotically moving surgical instruments having surgical end effectors at an internal surgical site within a patient.

FIGS. 6A-6B show an example manipulator arm in the pitch forward configuration and pitch back configurations, respectively.

FIG. 6C shows a graphical representation of the range of motion of the surgical instrument tool tip of an example manipulator arm, including a cone of silence or conical tool access limit zone in each of the pitch forward and pitch back configurations.

DETAILED DESCRIPTION OF THE INVENTION

Figure 1B:
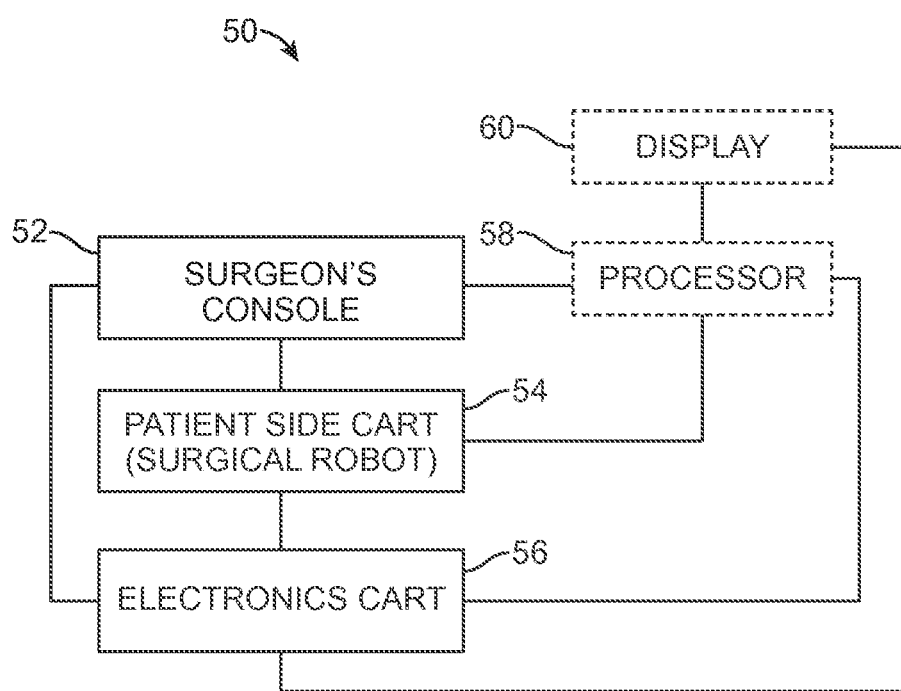
FIG. 1B diagrammatically illustrates the robotic surgical system of FIG. 1A.

The present invention generally provides improved surgical and robotic devices, systems, and methods. The invention is particularly advantageous for use with surgical robotic systems in which a plurality of surgical tools or instruments will be mounted on and moved by an associated plurality of robotic manipulators during a surgical procedure. The robotic systems will often comprise telerobotic, telesurgical, and/or telepresence systems that include processors configured as master-slave controllers. By providing robotic systems employing processors appropriately configured to move manipulator assemblies with articulated linkages having relatively large numbers of degrees of freedom, the motion of the linkages can be tailored for work through a minimally invasive access site.

The robotic manipulator assemblies described herein will often include a robotic manipulator and a tool mounted thereon (the tool often comprising a surgical instrument in surgical versions), although the term "robotic assembly" will also encompass the manipulator without the tool mounted thereon. The term "tool" encompasses both general or industrial robotic tools and specialized robotic surgical instruments, with these later structures often including an end effector which is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base which is fixed in space during at least a portion of a robotic procedure, and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

The end effector will typically move in the workspace with between two and six degrees of freedom. As used herein, the term "position" encompasses both location and orientation. Hence, a change in a position of an end effector (for example) may involve a translation of the end effector from a first location to a second location, a rotation of the end effector from a first orientation to a second orientation, or a combination of both. When used for minimally invasive robotic surgery, movement of the manipulator assembly may be controlled by a processor of the system so that a shaft or intermediate portion of the tool or instrument is constrained to a safe motion through a minimally invasive surgical access site or other aperture. Such motion may include, for example, axial insertion of the shaft through the aperture site into a surgical workspace, rotation of the shaft about its axis, and pivotal motion of the shaft about a pivot point adjacent the access site.

Many of the example manipulator assemblies described herein have more degrees of freedom than are needed to position and move an end effector within a surgical site. For example, a surgical end effector that can be positioned with six degrees of freedom at an internal surgical site through a minimally invasive aperture may in some embodiments have nine degrees of freedom (six end effector degrees of freedom—three for location, and three for orientation—plus three degrees of freedom to comply with the access site constraints), but will often have ten or more degrees of freedom. Highly configurable manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly within the null-space of the Jacobian.

The invention provides robotic linkage structures which are particularly well suited for surgical (and other) applications in which a wide range of motion is desired, and for which a limited dedicated volume is available due to the presence of other robotic linkages, surgical personnel and equipment, and the like. The large range of motion and reduced volume needed for each robotic linkage may also provide greater flexibility between the location of the robotic support structure and the surgical or other workspace, thereby facilitating and speeding up setup.

The term "state" of a joint or the like will often herein refer to the control variables associated with the joint. For example, the state of an angular joint can refer to the angle defined by that joint within its range of motion, and/or to the angular velocity of the joint. Similarly, the state of an axial or prismatic joint may refer to the joint's axial position, and/or to its axial velocity. While many of the controllers described herein comprise velocity controllers, they often also have some position control aspects. Alternative embodiments may rely primarily or entirely on position controllers, acceleration controllers, or the like. Many aspects of control system that can be used in such devices are more fully described in U.S. Pat. No. 6,699,177, the full disclosure of which is incorporated herein by reference. Hence, so long as the movements described are based on the associated calculations, the calculations of movements of the joints and movements of an end effector described herein may be performed using a position control algorithm, a velocity control algorithm, a combination of both, and/or the like.

In some embodiments, the tool of an exemplary manipulator arm pivots about a pivot point adjacent a minimally invasive aperture. In some embodiments, the system may utilize a hardware remote center, such as the remote center kinematics described in U.S. Pat. No. 6,786,896, the entire contents of which are incorporated herein by reference. Such systems may utilize a double parallelogram linkage which constrains the movement of the linkages such that the shaft of the instrument supported by the manipulator pivots about a remote center point. Alternative mechanically constrained remote center linkage systems are known and/or may be developed in the future. Surprisingly, work in connection with the present invention indicates that remote center linkage systems may benefit from highly configurable kinematic architectures. In particular when a surgical robotic system has a linkage that allows pivotal motion about two axes intersecting at or near a minimally invasive surgical access site, the spherical pivotal motion may encompass the full extent of a desired range of motion within the patient, but may still suffer from avoidable deficiencies (such as being poorly conditioned, being susceptible to arm-to-arm or arm-to-patient contact outside the patient, and/or the like). At first, adding one or more additional degrees of freedom that are also mechanically constrained to pivotal motion at or near the access site may appear to offer few or any improvements in the range of motion. Surprisingly, such joints can provide significant advantages by allowing the overall system to be configured in or driven toward a collision-inhibiting pose, by further extending the range of motion for other surgical procedures, and the like. In other embodiments, the system may utilize software to achieve a remote center, such as described in U.S. Pat. No. 8,004,229, the entire contents of which are incorporated herein by reference. In a system having a software remote center, the processor calculates movement of the joints so as to pivot an intermediate portion of the instrument shaft about a pivot point determined, as opposed to a mechanical constraint. By having the capability to compute software pivot points, different modes characterized by the compliance or stiffness of the system can be selectively implemented. More particularly, different system modes over a range of pivot points/centers (e.g., moveable pivot points, passive pivot points, fixed/rigid pivot point, soft pivot points) can be implemented as desired.

Despite the many advantages of a robotic surgical system having multiple highly configurable manipulators, since the manipulators include a relatively large number of joints and links between the base and instrument with redundant degrees of freedom, the commanded motion of the plurality of joints to achieve a desired movement of a distal end effector and/or the remote center may produce joint velocities that are undesirable, excessive kinetic energy associated with one or more joints, or may produce motion that does not meet a desired motion preference. Examples of undesirable joint velocities may include an undesirable combination of joint states, excessive joint velocities for one or more joints, or disproportional joints states. The present invention provides a desired movement, such as a combination of joints states or other such movement described herein, for the one or more joints during commanded end effector movement.

In one aspect, calculated null-space movement relating to various other objectives, such as an avoidance movements, commanded reconfiguration, desired manipulator poses or joint behaviors, may overlay the calculated joint velocities to achieve commanded end effector movement concurrent with achieving various other objectives. This may be achieved by utilizing a null-space manager system that consolidates null-space movements associated with multiple objectives so as to provide a null-space movement in accordance with the multiple objectives or at least in accordance with a desired relationship and/or behavior between the multiple objectives when such objectives conflict.

In certain aspects, the manipulator system is configured to determine each null-space objective function as a stand-alone software entity which assumes that each is the only objective in existence, assigns each objective function some useful attributes, and pipes the outputs of the individual objective functions into a null-space manager. The null-space manager typically include a processor of the system having programmable instructions recorded thereon for managing the objectives by performing the methods describes therein. The null-space manager may include one or more modes for managing null-space movements associated with different objectives according to any of the methods and approaches described herein. The attributes of the null-space objectives are then used by the manager in combining the multitude of inputs into a consolidated null-space command, which can then be combined with the null-perpendicular-space command and sent to the manipulator's joint controller. The manager may utilize various different approaches or algorithms in consolidating the multiple null-space objectives based on their respective attributes, which may include weighting, scaling, saturation levels, priorities between objectives, master velocity limiting, and saturated limited integrator algorithms, or various other features. In one aspect, null-space coefficients may be the multipliers for a set of null-space basis vectors.

Examples of such avoidance movements are described in U.S. Provisional Application No. 61/654,755 filed Jun. 1, 2012, entitled "Manipulator Arm-to-Patient Collision Avoidance Using a Null-Space;" and U.S. Provisional Application No. 61/654,773 filed Jun. 1, 2012, entitled "System and Methods for Avoiding Collisions Between Manipulator Arms Using a Null-Space," the disclosures of which are incorporated herein by reference in their entireties. Examples of a null-space objectives using commanded reconfiguration are described in U.S. Provisional Application No. 61/654,764 filed Jun. 1, 2012, entitled "Commanded Reconfiguration of a Surgical Manipulator Using the Null-Space," the disclosure of which is incorporated herein by reference in its entirety.

In the following description, various embodiments of the present invention will be described. For purposes of explanation, specific configurations and details are set forth in order to provide a thorough understanding of the embodiments. However, it will also be apparent to one skilled in the art that the present invention may be practiced without various specific details. Furthermore, well-known features may be omitted or simplified in order not to obscure the embodiment being described.

Referring now to the drawings, in which like reference numerals represent like parts throughout the several views, FIG. 1A is an overhead view illustration of a Minimally Invasive Robotic Surgical (MIRS) system 10, in accordance with many embodiments, for use in performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 so as to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

FIG. 1B diagrammatically illustrates a robotic surgery system 50 (such as MIRS system 10 of FIG. 1A). As discussed above, a Surgeon's Console 52 (such as Surgeon's Console 16 in FIG. 1A) can be used by a Surgeon to control a Patient Side Cart (Surgical Robot) 54 (such as Patent Side Cart 22 in FIG. 1A) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1A). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, and can be used to process the captured images. The images can also be processed by a combination the Electronics Cart 56 and the processor 58, and can be coupled together so as to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 2:
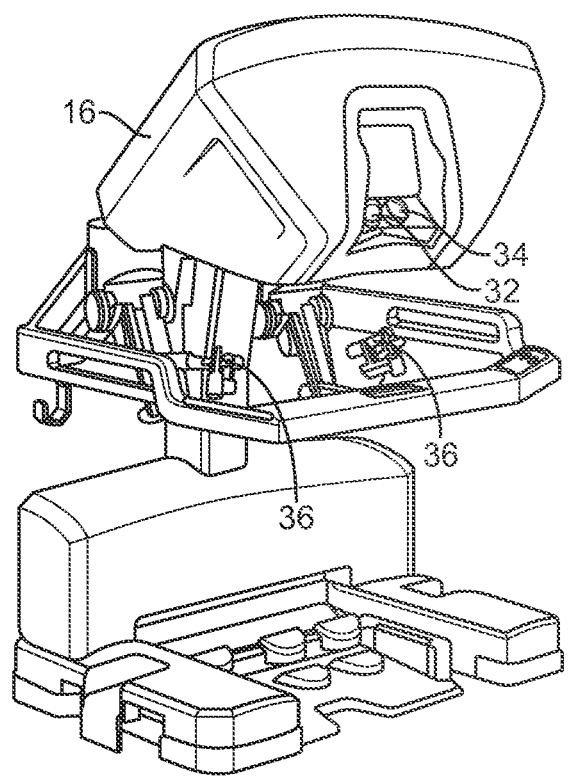
FIG. 2 is a perspective view illustrating a master surgeon console or workstation for inputting surgical procedure commands in the surgical system of FIG. 1A, the console including a processor for generating manipulator command signals in response to the input commands.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn causes the Patient Side Cart 22 (shown in FIG. 1A) to manipulate one or more tools. The input control devices 36 can provide the same degrees of freedom as their associated tools 26 (shown in FIG. 1A) so as to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
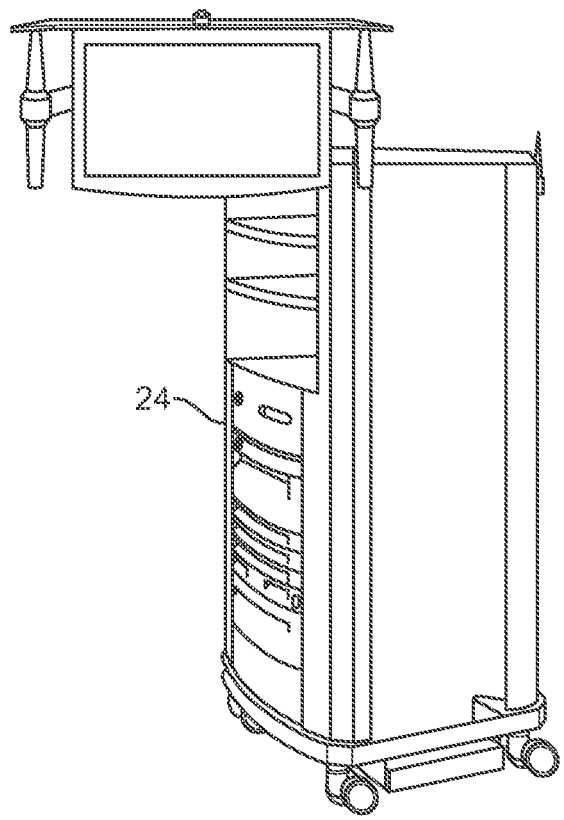
FIG. 3 is a perspective view of the electronics cart of FIG. 1A.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images so as to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations.

Figure 4:
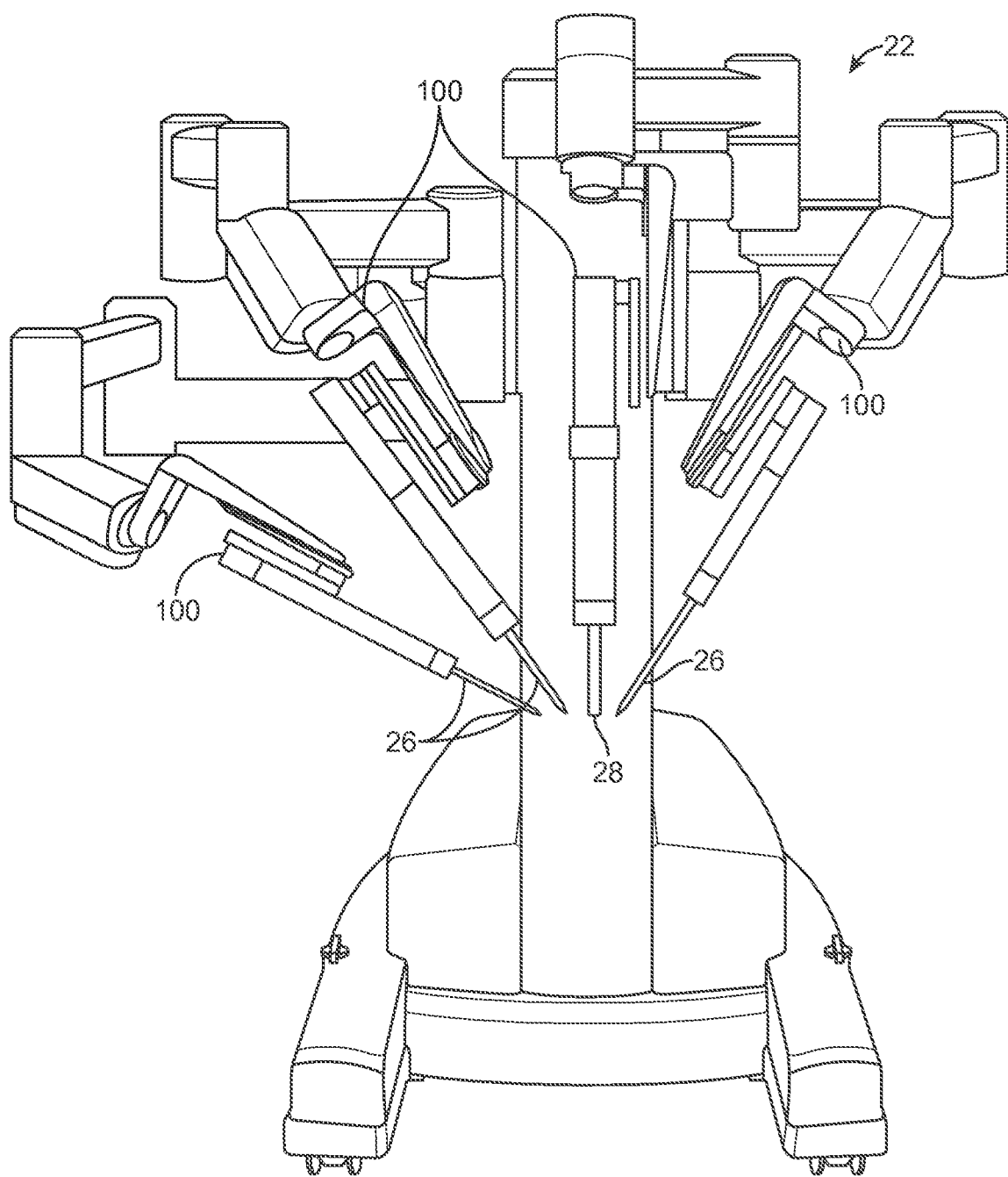
FIG. 4 is a perspective view of a patient side cart having four manipulator arms.

FIG. 4 shows a Patient Side Cart 22 having a plurality of manipulator arms, each supporting a surgical instrument or tool 26 at a distal end of the manipulator arm. The Patient Side Cart 22 shown includes four manipulator arms 100 which can be used to support either a surgical tool 26 or an imaging device 28, such as a stereoscopic endoscope used for the capture of images of the site of the procedure. Manipulation is provided by the robotic manipulator arms 100 having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical instruments or tools 26 when they are positioned within the field-of-view of the imaging device 28.

Regarding surgical tool 26, a variety of alternative robotic surgical tools or instruments of different types and differing end effectors may be used, with the instruments of at least some of the manipulators being removed and replaced during a surgical procedure. Several of these end effectors, including DeBakey Forceps, microforceps, Potts scissors, and clip applier include first and second end effector elements which pivot relative to each other so as to define a pair of end effector jaws. Other end effectors, including scalpel and electrocautery probe have a single end effector element. For instruments having end effector jaws, the jaws will often be actuated by squeezing the grip members of handle. Single end effector instruments may also be actuated by gripping of the grip members, for example, so as to energize an electrocautery probe.

The elongate shaft of instrument 26 allow the end effectors and the distal end of the shaft to be inserted distally into a surgical worksite through a minimally invasive aperture, often through an abdominal wall or the like. The surgical worksite may be insufflated, and movement of the end effectors within the patient will often be effected, at least in part, by pivoting of the instrument 26 about the location at which the shaft passes through the minimally invasive aperture. In other words, manipulators 100 will move the proximal housing of the instrument outside the patient so that shaft extends through a minimally invasive aperture location so as to help provide a desired movement of end effector. Hence, manipulators 100 will often undergo significant movement outside patient P during a surgical procedure.

Exemplary manipulator arms in accordance with many embodiments of the present invention can be understood with reference to FIGS. 5A-12C. As described above, a manipulator arm generally supports a distal instrument or surgical tool and effects movements of the instrument relative to a base. As a number of different instruments having differing end effectors may be sequentially mounted on each manipulator during a surgical procedure (typically with the help of a surgical assistant), a distal instrument holder will preferably allow rapid removal and replacement of the mounted instrument or tool. As can be understood with reference to FIG. 4, manipulators are proximally mounted to a base of the patient side cart. Typically, the manipulator arm includes a plurality of linkages and associated joints extending between the base and the distal instrument holder. In one aspect, an exemplary manipulator includes a plurality of joints having redundant degrees of freedom such that the joints of the manipulator arm can be driven into a range of differing configurations for a given end effector position. This may be the case for any of the embodiments of manipulator arms disclosed herein.

Figure 5A:
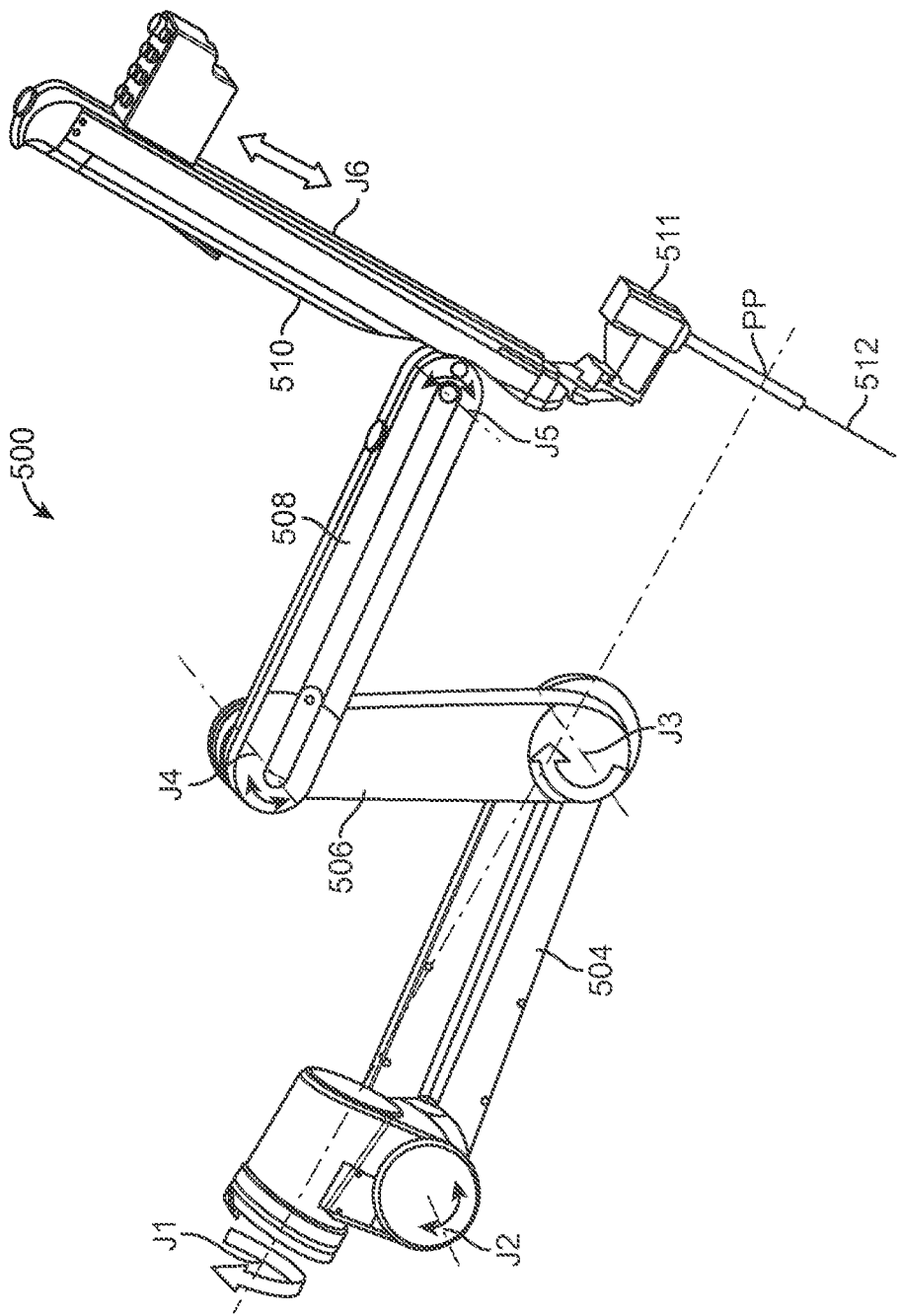
FIGS. 5A-5D show an example manipulator arm.

In many embodiments, such as shown for example in FIG. 5A, an exemplary manipulator arm includes a proximal revolute joint J1 that rotates about a first joint axis so as to revolve the manipulator arm distal of the joint about the joint axis. In some embodiments, revolute joint J1 is mounted directly to the base, while in other embodiments, joint J1 may be mounted to one or more movable linkages or joints. The joints of the manipulator, in combination, have redundant degrees of freedom such that the joints of the manipulator arm can be driven into a range of differing configurations for a given end effector position. For example, the manipulator arm of FIGS. 5A-5D may be maneuvered into differing configurations while the distal member 511 supported within the instrument holder 510 maintains a particular state and may include a given position or velocity of the end effector. Distal member 511 is typically a cannula through which the tool shaft 512 extends, and the instrument holder 510 is typically a carriage (shown as a brick-like structure that translates on a spar) to which the instrument attaches before extending through the cannula 511 into the body of the patient through the minimally invasive aperture.

Figure 5B:
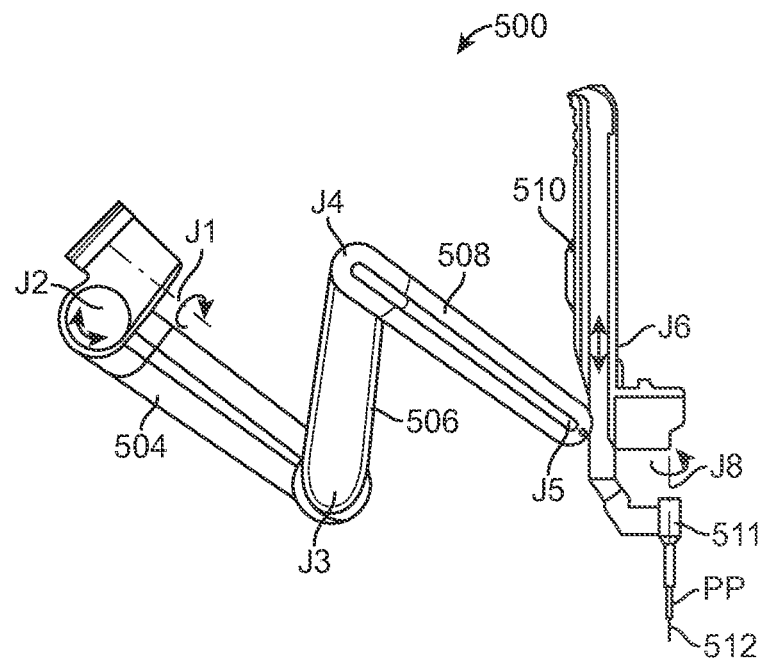
Figure 5D:
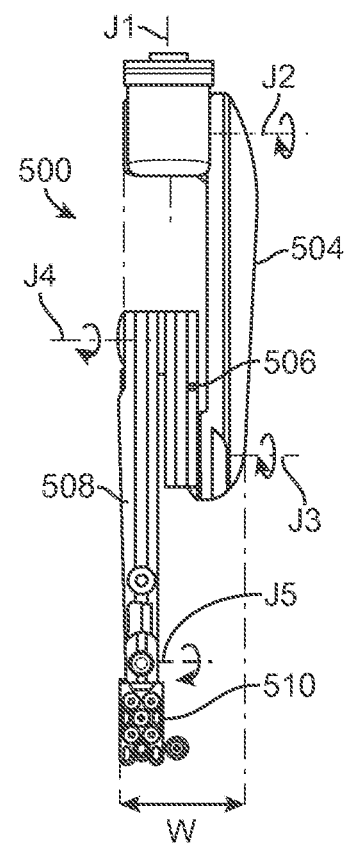
Figure 5C:
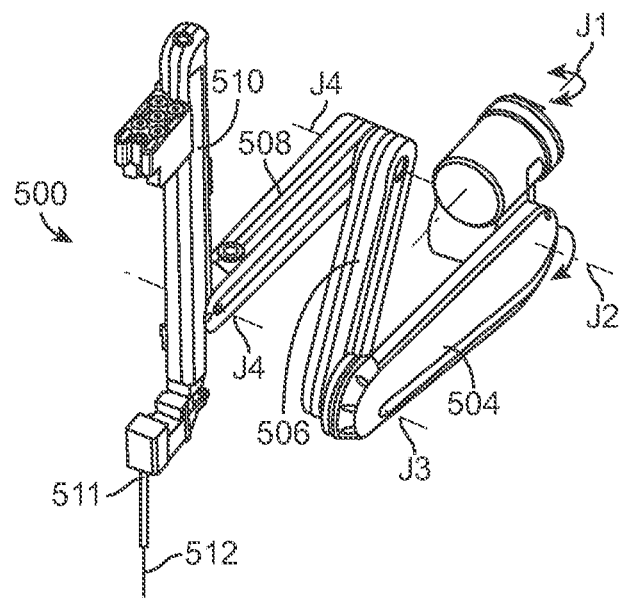

Describing the individual links of manipulator arm 500 of FIGS. 5A-5D along with the axes of rotation of the joints connecting the links as illustrated in FIG. 5A-5D, a first link 504 extends distally from a pivotal joint J2 which pivots about its joint axis and is coupled to revolute joint J1 which rotates about its joint axis. Many of the remainder of the joints can be identified by their associated rotational axes, as shown in FIG. 5A. For example, a distal end of first link 504 is coupled to a proximal end of a second link 506 at a pivotal joint J3 that pivots about its pivotal axis, and a proximal end of a third link 508 is coupled to the distal end of the second link 506 at a pivotal joint J4 that pivots about its axis, as shown. The distal end of the third link 508 is coupled to instrument holder 510 at pivotal joint J5. Typically, the pivotal axes of each of joints J2, J3, J4, and J5 are substantially parallel and the linkages appear "stacked" when positioned next to one another, as shown in FIG. 5D, so as to provide a reduced width w of the manipulator arm and improve patient clearance during maneuvering of the manipulator assembly. In many embodiments, the instrument holder also includes additional joints, such as a prismatic joint J6 that facilitates axial movement of instrument 306 through the minimally invasive aperture and facilitates attachment of the instrument holder to a cannula through which the instrument is slidably inserted.

The distal member or cannula 511 through which the tool 512 extends may include additional degrees of freedom distal of instrument holder 510. Actuation of the degrees of freedom of the instrument will often be driven by motors of the manipulator, and alternative embodiments may separate the instrument from the supporting manipulator structure at a quickly detachable instrument holder/instrument interface so that one or more joints shown here as being on the instrument are instead on the interface, or vice versa. In some embodiments, cannula 511 includes a rotational joint J7 (not shown) near or proximal of the insertion point of the tool tip or the pivot point PP, which generally is disposed at the site of a minimally invasive aperture. A distal wrist of the instrument allows pivotal motion of an end effector of surgical tool 512 about instrument joints axes of one or more joints at the instrument wrist. An angle between end effector jaw elements may be controlled independently of the end effector location and orientation.

The range of motion of an exemplary manipulator assembly can be appreciated by referring to FIGS. 6A-6C. During a surgical procedure, an exemplary manipulator arm can be maneuvered into a pitch forward configuration, as shown in FIG. 6A, or into a pitch back configuration, as shown in FIG. 6B, as needed to access particular patient tissues within a surgical workspace. A typical manipulator assembly includes an end effector that can pitch forwards and backwards about an axis by at least ±60 degrees, preferably by about ±75 degrees, and can also yaw about an axis by ±80 degrees. Although this aspect allows for increased maneuverability of the end effector with the assembly, there may be configurations in which movement of the end effector may be limited, particularly when the manipulator arm is in the full pitch forward or full pitch back configuration as in FIGS. 6A and 6B. In one embodiment, the manipulator arm has a Range of Motion (ROM) of (+/−75 deg) for the outer pitch, and (+/−300 degrees) for the outer yaw joints, respectively. In some embodiments, the ROM may be increased for the outer pitch to provide a ROM larger than (+/−90 deg) in which case a cone of space in which joint movement is limited or impossible could be made to disappear entirely, although generally the inner sphere associated with insertion limitations would remain. It is appreciated that various embodiments may be configured to have increased or decreased ROM, that the above noted ROMs are provided for illustrative purposes, and further that the invention is not limited to the ROMs described herein.

FIG. 6C graphically represents the overall range of motion and workspace of the tool tip of the exemplary manipulator of FIGS. 5A-5B. Although the workspace is shown as hemisphere, it may also be represented as a sphere depending on the range of motion and configuration of one or more revolute joints of the manipulator, such as joint J1. As shown, the hemisphere in FIG. 6C includes a central, small spherical void as well as two conical voids. The voids represent the areas in which movement of the tool tip may be impossible due to mechanical constraints or unfeasible due to extremely high joint velocities that make movement of the end effector difficult or slow. For these reasons, the conical void are referred to as the "cone of silence." In some embodiments, the manipulator arm may reach a singularity at a point within the cone. Since movement of the manipulator within or near the cone of silence may be impaired, it can be difficult to move the manipulator arm away from the cone of silence without manually moving one or more links of the manipulator to reconfigure the linkages and joints of the manipulator, which may require an alternative operating mode and delays the surgical procedure.

Movement of the instrument shaft into or near these conical portions typically occurs when the angle between distal linkages in the manipulator is relatively small. Thus, such configurations can be avoided by various null-space objectives, such as anisotropically emphasizing movement of the manipulator so as to increase the angles between linkages (so that the linkages are moved into a more orthogonal position relative to each other). For example, in the configurations shown in FIGS. 6A and 6B, when the angle between the distal most link and the instrument holder (angle a) becomes relatively small movement of the manipulator may become more difficult. Depending on the range of joint movements in the remaining joints in various embodiments, when the angle between certain linkages decreases, movement of the manipulator may be inhibited and in some cases, the manipulator arm may no longer be redundant. A manipulator configuration in which the instrument shaft nears these conical portions, or in which the angles between linkages are relatively low is said to be "poorly conditioned" such that maneuverability and dexterity of the manipulator arm is limited. It is desirable that the manipulator be "well conditioned" so as to maintain dexterity and range of movement. In one aspect, the present invention allows a user to avoid movement of the instrument shaft near the above described conical portions by simply entering a command to reconfigure the manipulator as desired, even during movement of the end effector in a surgical procedure. This aspect is particularly useful should the manipulator, for whatever reason, become "poorly conditioned."

While the embodiments of the manipulator described above may be utilized in the present invention, some embodiments may include additional joints, which may also be used to improve dexterity and the conditioning of the manipulator arm. For example, an exemplary manipulator may include a revolute joint and/or linkage proximal of joint J1 which can be used to revolve the manipulator arm of FIG. 5A, and its associated cone of silence, about an axis of the revolute joint so as to reduce or eliminate the cone of silence. In another embodiment, the exemplary manipulator may also include a distal pivotal joint that pivots the instrument holder about an axis substantially perpendicular to joint J5, thereby offsetting the tool tip so as to further reduce the cone of silence and improve the range of movement of the surgical tool. In still another embodiment, a proximal joint of the manipulator arm, such as J1, may be movably mounted on the base, so as to move or shift the cone of silence as needed and improve the range of motion of the manipulator tool tip. The use and advantages of such additional joints can be understood by referring to FIGS. 7A-12C, which illustrate examples of such joints, which may each be used independent of one another or used in combination, in any of the exemplary manipulator arms described herein.

Figure 7A:
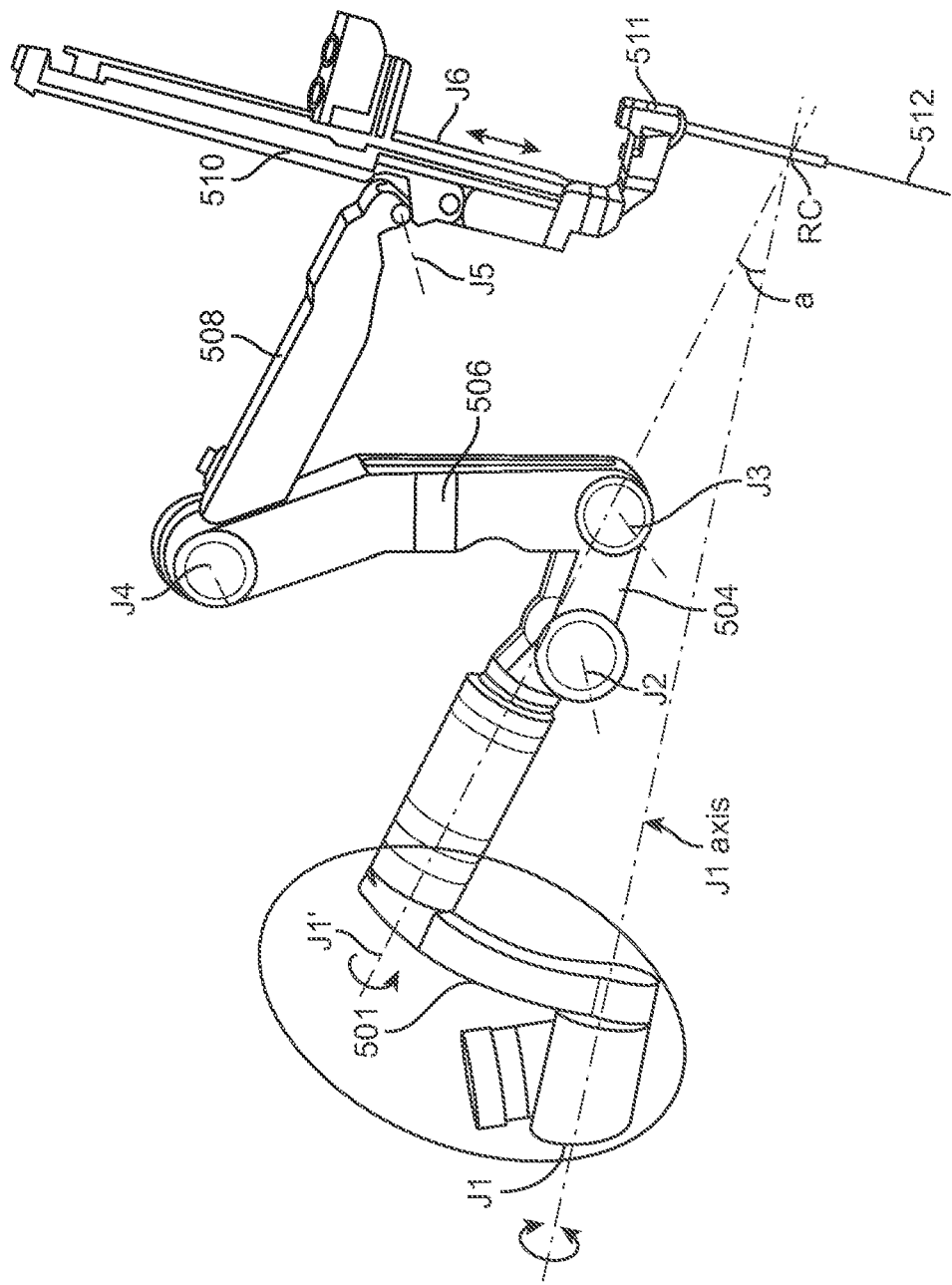
FIG. 7A shows example manipulator arms having a proximal revolute joint that revolves the manipulator arm about an axis of a proximal revolute joint.
Figure 7B:
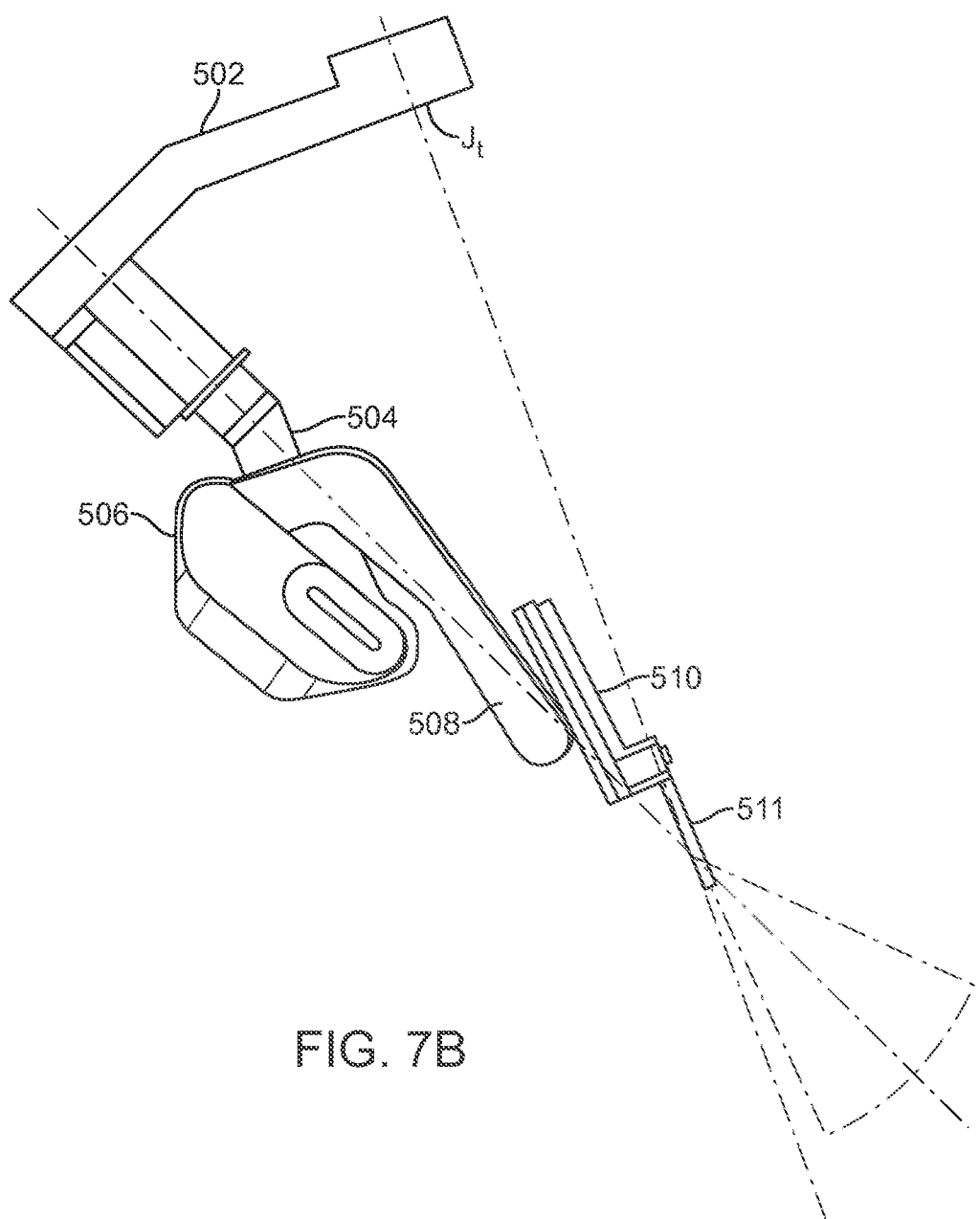
FIG. 7B shows an example manipulator arm and the associated range of motion and cone of silence, the exemplary manipulator arm having a proximal revolute joint that revolves the manipulator arm around an axis of a proximal revolute joint the movement of which can be used to mitigate the depicted cone of silence.

FIGS. 7A-7B illustrate an additional redundant joint for use with exemplary manipulator arms—a first joint coupling a proximal portion of the manipulator arm to the base. The first joint is a proximal revolute joint J1 that revolves the manipulator arm about a joint axis of joint J1. The proximal revolute J1 includes a link 501 that offsets joint J1' from the proximal revolute J1 by a pre-determined distance or angle. The link 501 can be a curved linkage, as shown in FIG. 7A, or a linear or angled linkage, as shown in FIG. 7B. Typically, the joint axis of the joint J1 is aligned with the remote center RC or insertion point of the tool tip, as shown in each of FIG. 7A. In an exemplary embodiment, the joint axis of joint J1 passes through the remote center, as does each other revolute joint axis in the manipulator arm, to prevent motion at the body wall and can therefore be moved during surgery. The axis of joint J1 is coupled to a proximal portion of the arm so it can be used to change the position and orientation of the back of the arm. In general, redundant axes, such as this, allow the instrument tip to follow the surgeon's commands while simultaneously avoiding collisions with other arms or patient anatomy. In one aspect, the proximal revolute J1 is used solely to change the mounting angle of the manipulator with respect to the floor. This angle is important in order to 1) avoid collisions with external patient anatomy and 2) reach anatomy inside the body. Typically, the angle a between the proximal link of the manipulator attached to the proximal revolute joint J1 and the axis of the proximal revolute is about 15 degrees.

FIG. 7B illustrates the relationship of the proximal revolute joint J1 and its associated joint axis and the cone of silence in an exemplary manipulator arm. The joint axis of the proximal revolute joint J1 may pass through the cone of silence or may be completely outside of the cone of silence. By revolving the manipulator arm about the axis of the proximal revolute J1, the cone of silence can be reduced (in an embodiment where the joint J1 axis passes through the cone of silence), or can be effectively eliminated (in an embodiment where the proximal revolute joint axis extends completely outside the cone of silence). The distance and angle of the link 501 determines the position of the joint J1 axis relative to the cone of silence.

Figure 8:
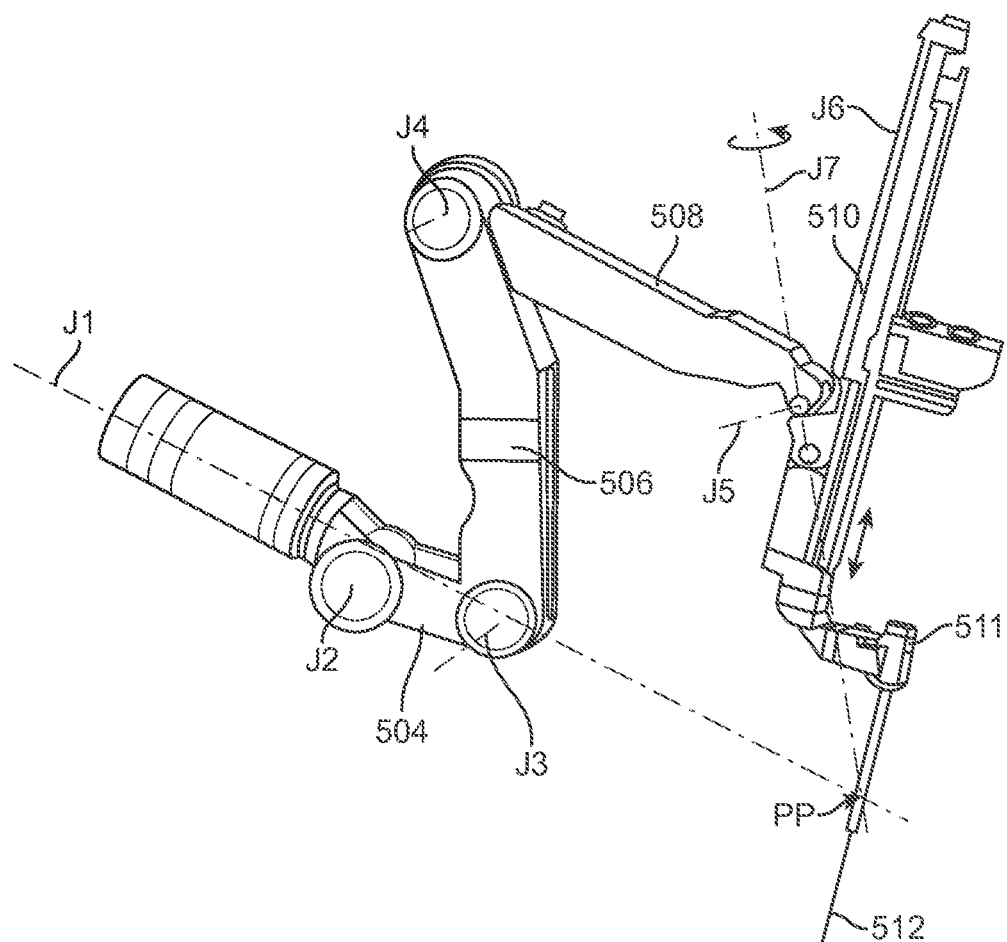
FIG. 8 shows an example manipulator arm having a revolute joint near the distal instrument holder.
Figure 9:
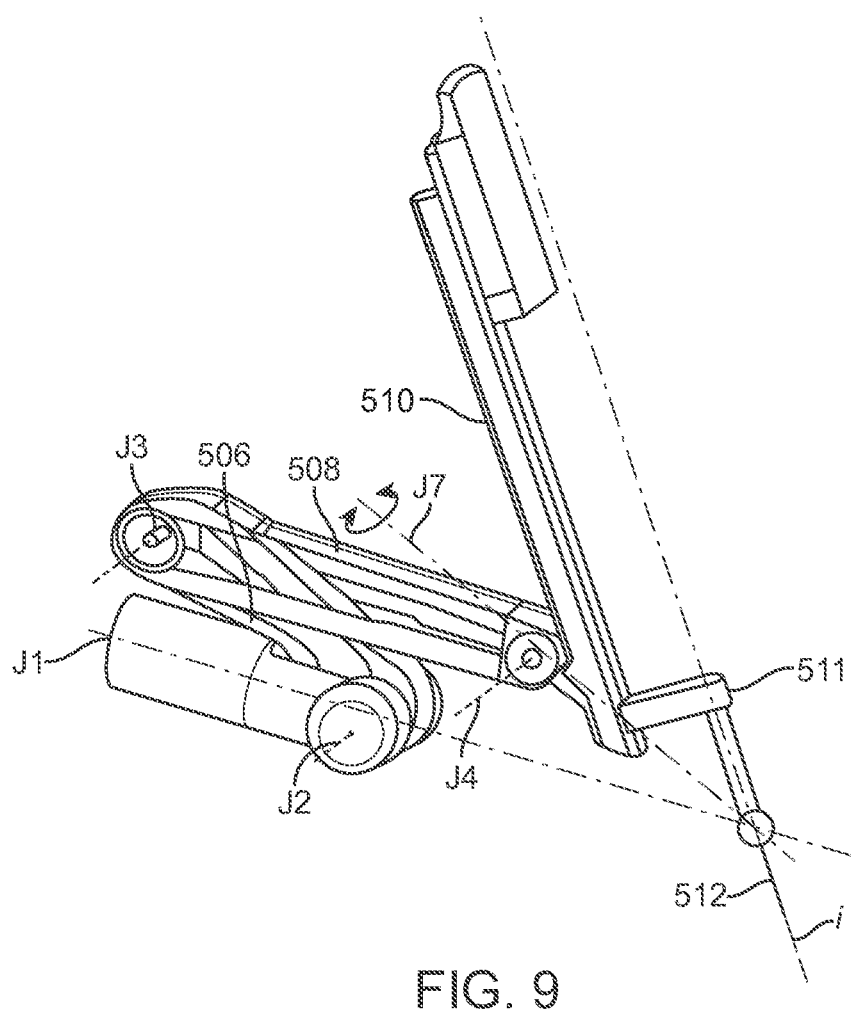
FIG. 9 shows an example manipulator arm having a revolute joint near the distal instrument holder that revolves or twists the instrument holder about the joint axis.
Figure 10A:
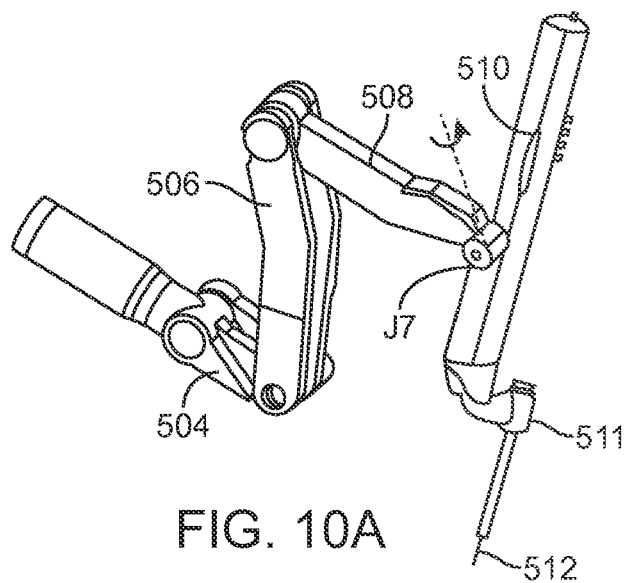
FIGS. 10A-10C show sequential views of an exemplary manipulator arm having a revolute joint near a distal instrument holder as the joint is moved throughout its range of joint movement.
Figure 10B:
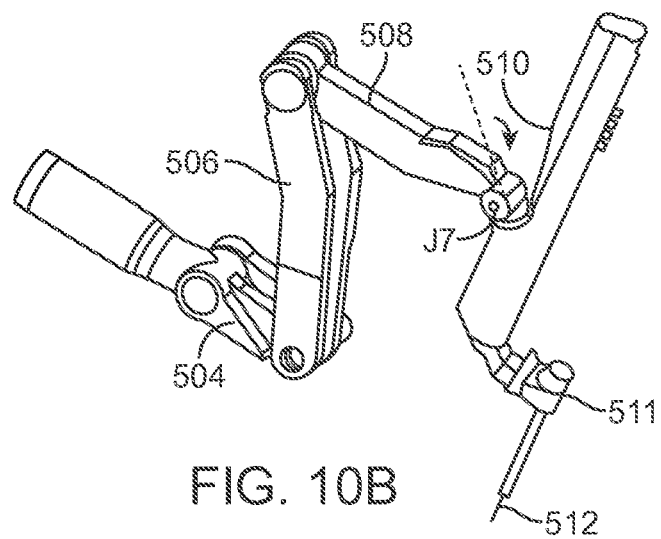
Figure 10C:
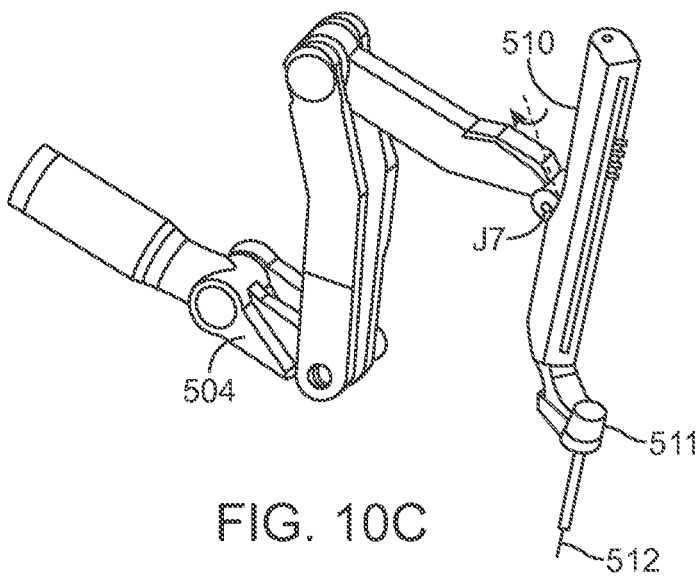

FIG. 8 illustrates another type of redundant joint for use with exemplary manipulator arms, a distal revolute joint J7 coupling the instrument holder 510 to a distal link of the manipulator arm 508. The distal revolute joint J7 allows the system to twist the instrument holder 510 about the joint axis, which typically passes through the remote center or insertion point. Ideally, the revolute joint is located distally on the arm and is therefore particularly well suited to moving the orientation of the insertion axis. The addition of this redundant axis allows the manipulator to assume multiple positions for any single instrument tip position. In general, redundant axes, such as this, allow the instrument tip to follow the surgeon's commands while simultaneously avoiding collisions with other arms or patient anatomy. Because the distal revolute joint J7 has the ability to move the insertion axis closer to the yaw axis, it is able to increase arm pitch back range of motion. The relationship between the axis of the distal revolute joint J7, the yaw axis of J1' and the insertion axis of tool tip is shown in FIG. 9. FIGS. 10A-10C show the sequential movement of the J7 and how it shifts the insertion axis of tool tip from side to side.

Figure 11A:
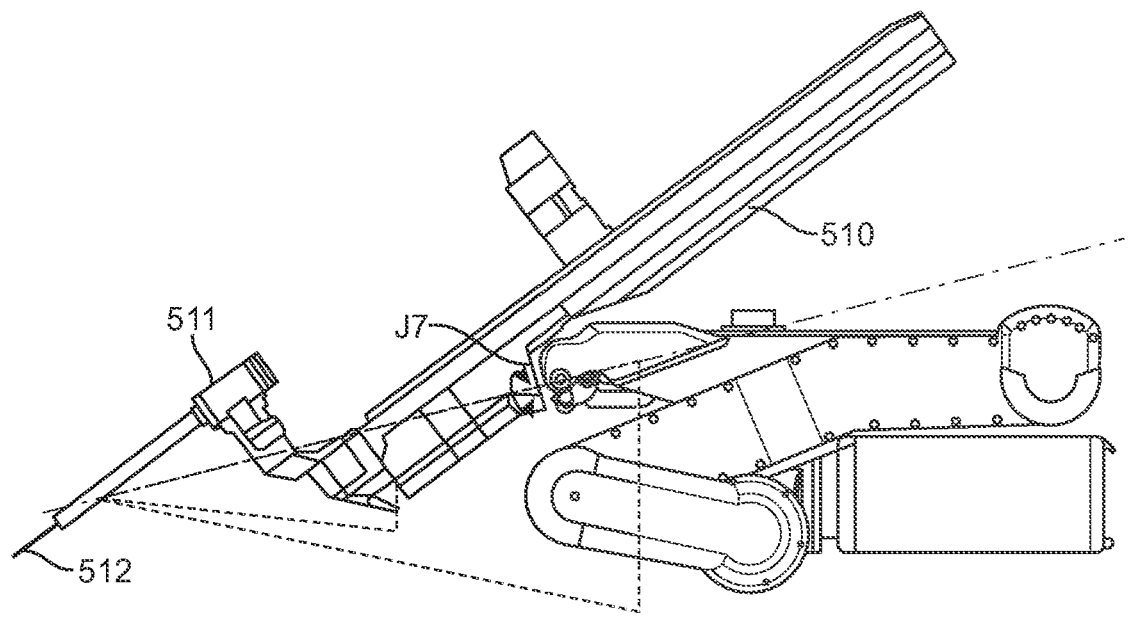
FIGS. 11A-11B show the revolved profile of an exemplary manipulator arm having a distal revolute joint when the angular displacement of the joint is 0° versus an angular displacement of 90°, respectively.
Figure 11B:
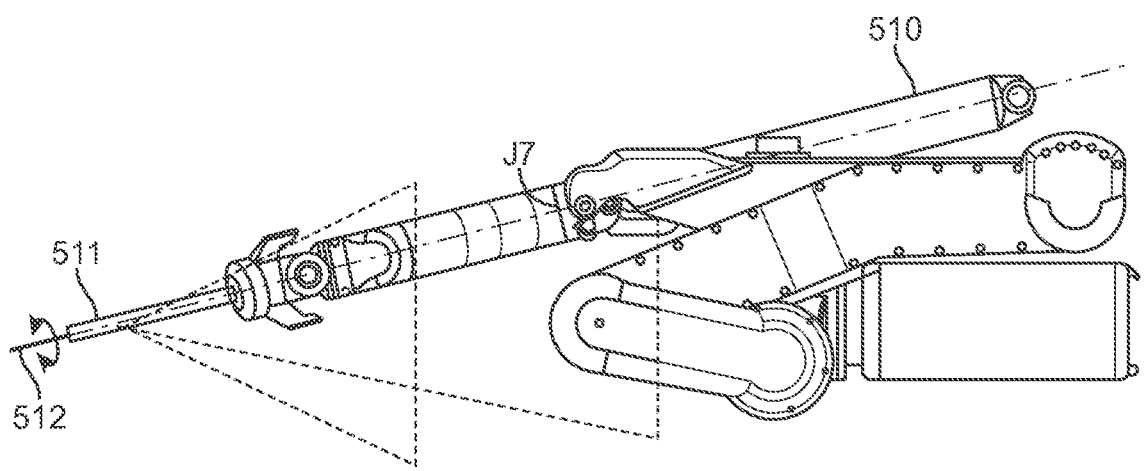

Another advantage of the distal revolute joint J7 is that it may reduce the patient clearance cone, which is the swept volume of the distal portion of the manipulator arm proximal of the insertion point which must clear the patient to avoid collision between the patient and the instrument holder or distal linkages of the manipulator arm. FIG. 11A illustrates the patient clearance cone of the proximal portion of the manipulator arm while the angular displacement of the distal revolute joint remains at 0°. FIG. 11B illustrates the reduced patient clearance cone of the proximal portion of the manipulator arm while the distal revolute joint is shown having an angular displacement of 90° about its axis. Thus, in procedures having minimal patient clearance near the insertion point, use of the joint J7 in accordance with the present invention may provide additional clearance while maintaining the remote center location or the position of the end effector as desired.

Figure 12A:
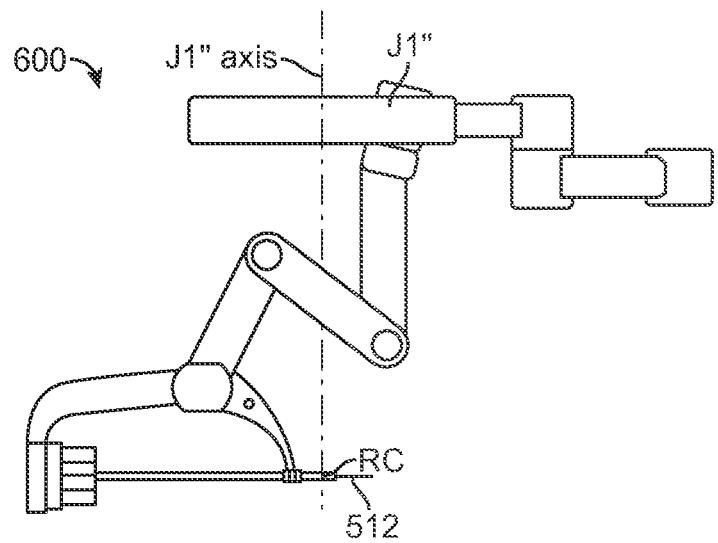
FIGS. 12A-12C show exemplary manipulator arms having a proximal joint that translates a proximal joint supporting the manipulator arm about a path of the joint.
Figures 12B, 12C:
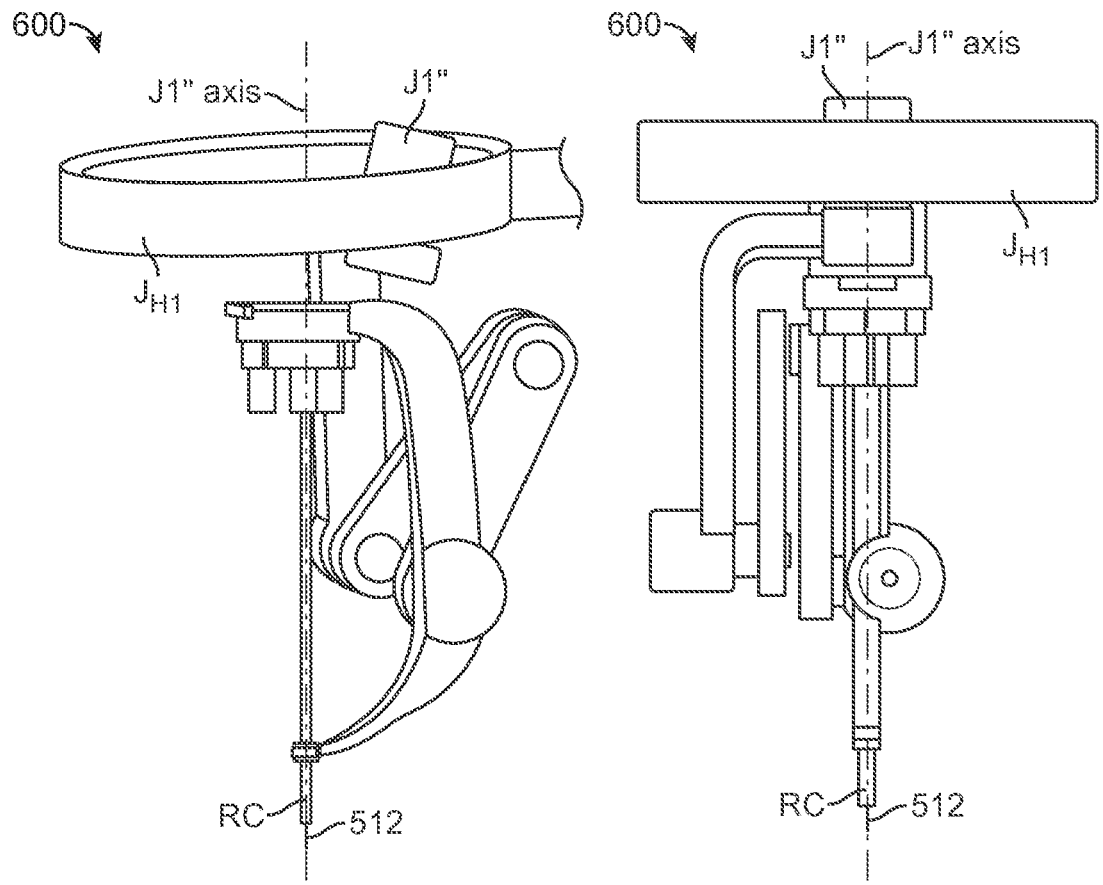

FIGS. 12A-12C illustrate another type of redundant joint for use with exemplary manipulator arms, a proximal joint that translates or revolves the manipulator arm about an axis. In many embodiments, this proximal translatable joint translates a proximal joint of the manipulator, such as joint J1 or J1', along a path so as to reduce or eliminate the cone of silence by shifting or rotating the range of motion of the manipulator arm to provide for better conditioning and improved maneuverability of the manipulator arm. The translatable joint may include a circular path, such as shown in joint J1" in FIGS. 12A-12D, or may include a semi-circular or arcuate path. Generally, the joint revolves the manipulator arm about an axis of the translatable joint that intersects with the remote center RC about which the shaft of the tool 512 extending through cannula 511 pivots. In the embodiments shown this axis of J1" is a vertical axis, although in various other embodiments the axis may be at an angle or horizontal.

In some embodiments, the manipulator arm 500 may include any or all of the proximal and distal revolute joint, a proximal translatable joint and a parallelogram configuration of the distal linkages. Use of any or all of these features provide additional redundant degrees of freedom and facilitate reconfiguration in accordance with the present invention so as to provide for a better "conditioned" manipulator assembly by increasing the angles between linkages thereby improving the dexterity and motion of the manipulator. The increased flexibility of this exemplary manipulator can also be used to optimize the kinematics of the manipulator linkage so as to avoid joint limits, singularities, and the like.

In an example embodiment, the joint movements of the manipulator are controlled by driving one or more joints by a controller using motors of the system, the joints being driven according to coordinated and joint movements calculated by a processor of the controller. Mathematically, the controller may perform at least some of the calculations of the joint commands using vectors and/or matrices, some of which may have elements corresponding to configurations or velocities of the joints. The range of alternative joint configurations available to the processor may be conceptualized as a joint space. The joint space may, for example, have as many dimensions as the manipulator has degrees of freedom, and a particular configuration of the manipulator may represent a particular point in the joint space, with each coordinate corresponding to a joint state of an associated joint of the manipulator.

In an example embodiment, the system includes a controller in which a commanded position and velocity of a feature in the work-space, denoted here as its Cartesian space, are inputs. The feature may be any feature on the manipulator or off the manipulator which can be used as a control frame to be articulated using control inputs. An example of a feature on the manipulator, used in many examples described herein, would be the tool-tip. Another example of a feature on the manipulator would be a physical feature which is not on the tool-tip, but is a part of the manipulator, such as a pin or a painted pattern. An example of a feature off the manipulator would be a reference point in empty space which is exactly a certain distance and angle away from the tool-tip. Another example of a feature off the manipulator would be a target tissue whose position relative to the manipulator can be established. In all these cases, the end effector is associated with an imaginary control frame which is to be articulated using control inputs. However, in the following, the "end effector" and the "tool tip" are used synonymously. Although generally, there is no closed form relationship which maps a desired Cartesian space end effector position to an equivalent joint-space position, there is generally a closed form relationship between the Cartesian space end effector and joint-space velocities. The kinematic Jacobian is the matrix of partial derivatives of Cartesian space position elements of the end effector with respect to joint space position elements. In this way, the kinematic Jacobian captures the kinematic relationship between the end effector and the joints. In other words, the kinematic Jacobian captures the effect of joint motion on the end effector. The kinematic Jacobian (J) can be used to map joint-space velocities (dq/dt) to Cartesian space end effector velocities (dx/dt) using the relationship below:

$$dx/dt = J dq/dt$$

Thus, even when there is no closed-form mapping between input and output positions, mappings of the velocities can iteratively be used, such as in a Jacobian-based controller to implement a movement of the manipulator from a commanded user input, however a variety of implementations can be used. Although many embodiments include a Jacobian-based controller, some implementations may use a variety of controllers that may be configured to access the Jacobian of the manipulator arm to provide any of the features described herein.

One such implementation is described in simplified terms below. The commanded joint position is used to calculate the Jacobian (J). During each time step ($\Delta t$) a Cartesian space velocity (dx/dt) is calculated to perform the desired move ($dx_{des}/dt$) and to correct for built up deviation ($\Delta x$) from the desired Cartesian space position. This Cartesian space velocity is then converted into a joint-space velocity (dq/dt) using the pseudo-inverse of the Jacobian ($J^\#$). The resulting joint-space commanded velocity is then integrated to produce joint-space commanded position (q). These relationships are listed below:

$$dx/dt = dx_{des}/dt + k\Delta x \quad (1)$$

$$dq/dt = J^\# dx/dt \quad (2)$$

$$q_i = q_{i-1} + dq/dt \Delta t \quad (3)$$

The pseudo-inverse of the Jacobian (J) directly maps the desired tool tip motion (and, in some cases, a remote center of pivotal tool motion) into the joint velocity space. If the manipulator being used has more useful joint axes than tool tip degrees of freedom (up to six), (and when a remote center of tool motion is in use, the manipulator should have an additional 3 joint axes for the 3 degrees of freedom associated with location of the remote center), then the manipulator is said to be redundant. A redundant manipulator's Jacobian includes a "null-space" having a dimension of at least one. In this context, the "null-space" of the Jacobian (N(J)) is the space of joint velocities which instantaneously achieves no tool tip motion (and when a remote center is used, no motion of the pivotal point location); and "null-motion" is the combination, trajectory or path of joint positions which also produces no instantaneous movement of the tool tip and/or location of the remote center. Incorporating or injecting the calculated null-space velocities into the control system of the manipulator to achieve the desired reconfiguration of the manipulator (including any reconfigurations described herein) changes above equation (2) to the following:

$$dq/dt = dq_{perp}/dt + dq_{null}/dt \quad (4)$$

$$dq_{perp}/dt = J^\# dx/dt \quad (5)$$

$$dq_{null}/dt = (1 - J^\# J)z = V_n V_n^T z = V_n \alpha \quad (6)$$

Alternatively, in certain aspects, an augmented Jacobian that incorporates a potential function gradient and is applied to the Cartesian Space end effector velocities may be used. The augmentation of the Jacobian calculates the joint velocities as desired. It is understood that in referring to calculating joint movements using the Jacobian, such calculations may include the augmented Jacobian approach. In accordance with the augmented Jacobian approach, the following equations may be used, although it is appreciated that column vectors may be used:

$$dx/dt = J*dq/dt$$

$$y = h(q)$$

$$dy/dt = \partial h/\partial q * dq/dt$$

$$[dx/dt^T dy/dt^T]^T = [J^T \partial h/\partial q^T]^T * dq/dt$$

$$d(x;y)/dt = [J;h']*dq/dt$$

$$dq/dt = [J;h']^\# d(x;y)/dt$$

In one example, set y=h(q) the complex network of potential field functions. dy/dt=∂h/∂q*dq/dt. dy/dt and ∂h/∂q and dy/dt can be dictated as desired based on the potential field functions, and the augmented equation would produce the combined desired result of both driving the end effector and tracking the paths in joint space.

The joint velocity according to Equation (4) has two components: the first being the null-perpendicular-space component, the "purest" joint velocity (shortest vector length) which produces the desired tool tip motion (and when the remote center is used, the desired remote center motion) and the second being the null-space component. Equations (2), (4), and (5) show that without a null-space component, the same equation is achieved. Equation (6) starts with a traditional form for the null-space component on the left, and on the far right side, shows the form used in an exemplary system, wherein $V_n$ is the set of orthonormal basis vectors for the null-space, and a are the coefficients for blending those basis vectors. In some embodiments, $\alpha$ is determined by control parameters, variables or setting, such as by use of knobs or other control means, to shape or control the motion within the null-space as desired.

Figure 13A:
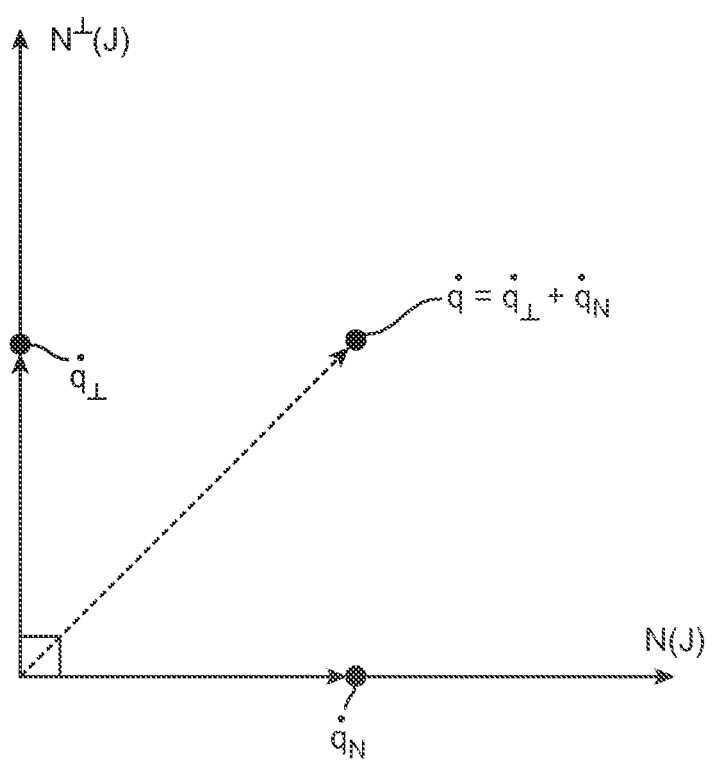
FIGS. 13A-13B graphically represent the relationship between the null-space and the null-perpendicular-space of the Jacobian of an example manipulator assembly.
Figure 13B:
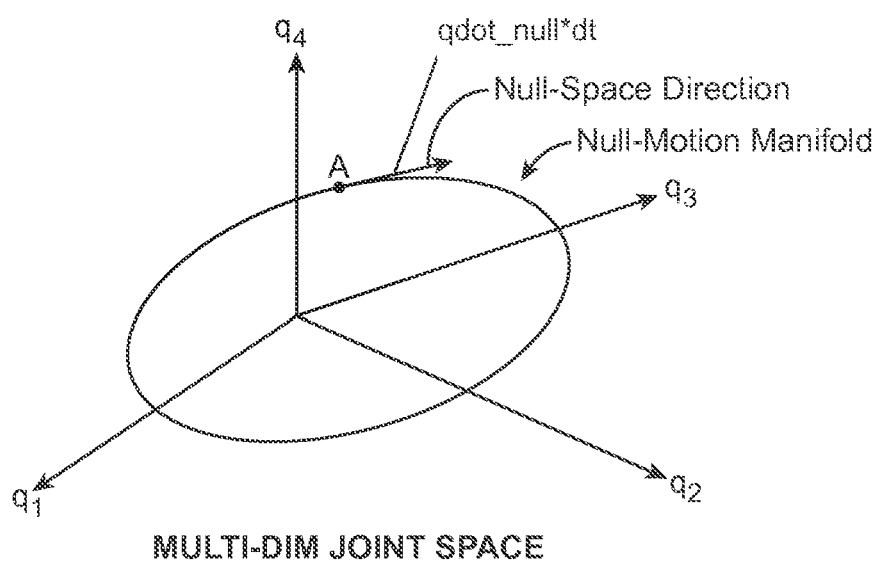

FIGS. 13A-13B graphically illustrate the relationship between the null-space of the Jacobian and the null-perpendicular-space of the Jacobian of an exemplary manipulator arm. FIG. 13A shows a two-dimensional schematic showing the null-space along the horizontal axis, and the null-perpendicular-space along the vertical axis, the two axes being orthogonal to one another. The diagonal vector represents the sum of a velocity vector in the null-space and a velocity vector in the null-perpendicular-space, which is representative of Equation (4) above.

FIG. 13B graphically illustrates the relationship between the null-space and the null-motion manifold within a four-dimensional joint space, shown as the "null-motion manifold." Each arrow (q1, q2, q3, and q4) representing a principal joint axis. The closed curve represents a null-motion manifold which is a set of joint-space positions which instantaneously achieves the same end effector position. For a given point A on the curve, since the null-space is a space of joint velocities which instantaneously produce no movement of the end effector, the null-space is parallel to the tangent of the null-motion manifold at point A.

Figure 14A:
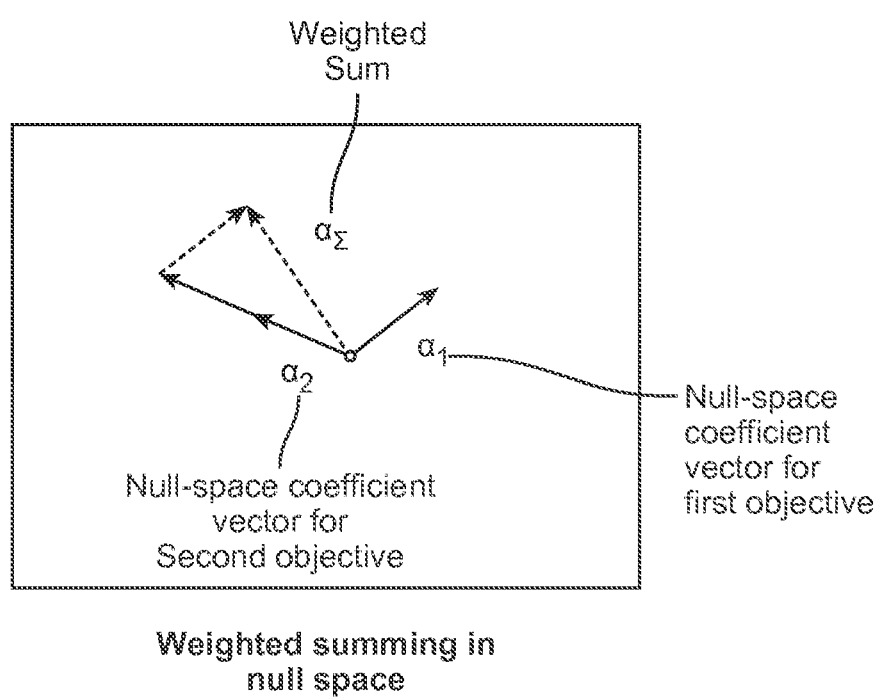
FIGS. 14A-14D graphically depict the different approaches of consolidating multiple null-space objectives using a manager in accordance with certain embodiments.
Figure 14B:
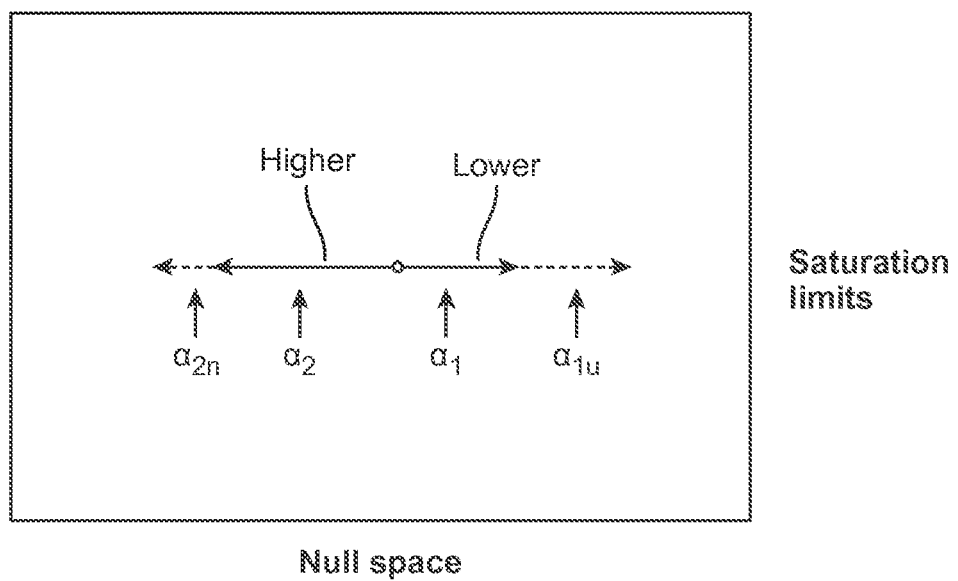
Figure 14C:
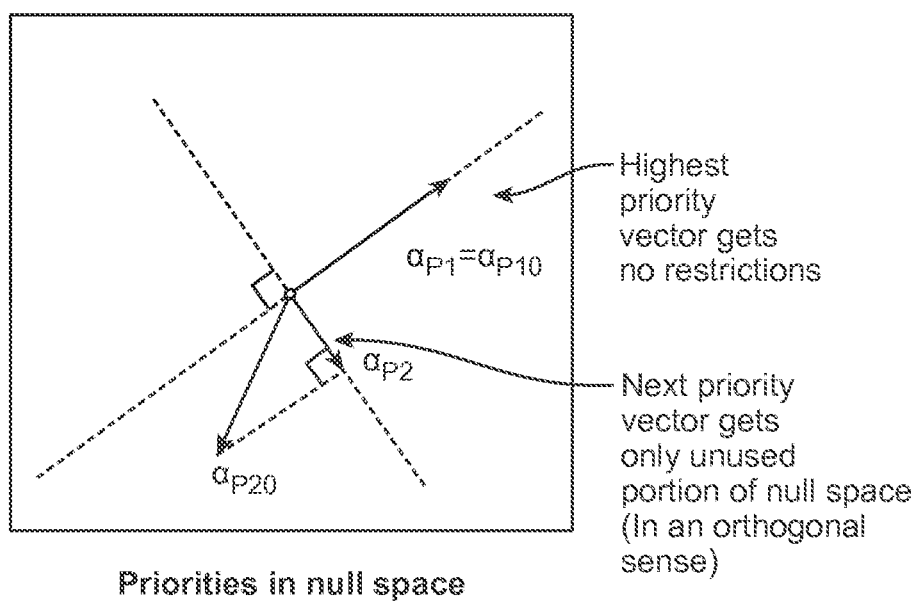

FIGS. 14A-14D graphically illustrates various approaches of consolidating multiple objectives with a null-space manager in accordance with embodiments of the present invention. FIG. 14A relates to weighted summing of multiple objectives; FIG. 14B relates to saturation limits of the multiple objectives; FIG. 14C relates to priorities of multiple objectives in the null-space; and FIG. 14D relates to management of multiple objectives in relation to the walls or borders of the joint space. In certain aspects, a null-space manager is used to manage multiple null-space objectives by determining null-space coefficients ($\alpha$) for each null-space objective function, and consolidating the null-space coefficients using any of the following attributes (or combinations thereof) for each objective:

(a) Weighting: This attribute is used in a weighted summing paradigm, which allows a scaled blending of multiple features or objectives. For example, if a user desires an emphasis of the null-space usage for an extended pitch-back objective to be twice as much as that for arm-to-arm collision avoidance objective, then the weight of the former would be set to be twice that of the latter. Such an example is shown in FIG. 14A, which illustrates a null-space coefficient vector for the first objective, $\alpha_1$, and a null-space coefficient vector for a second objective, $\alpha_2$. To determine a null-space movement in which second objective is weighted twice that as the first, the null-space coefficient vector for the second objective is doubled before summing with the null-space coefficient vector of the first objective, $\alpha_1$, such that the resulting sum, $\alpha_\Sigma$, represents a null-space coefficient that emphasizes the second objective twice as much as the first objective when used in calculation of the null-space movement. It is appreciated that such weightings could be applied to various other management approaches involving various other attributes. This includes weights applied directly to the null-space vectors, rather than merely the coefficients of basis vectors.

(b) Saturation level: This attribute allows for management between multiple null-space objectives that may conflict or cancel one another other out. As noted above, the number of objective functions may be larger than the dimension of the null-space. In these cases (and sometimes in less dimensionally stringent cases too), multiple objective functions can produce null-space outputs which directly oppose each other. An example of this aspect is shown in FIG. 14B, which shows null-space coefficient vectors, $\alpha_{1u}$ and $\alpha_{2u}$, that are directly opposed. If these objective functions are summed without intervention, their result becomes zero which results in no beneficial action taken for either objective function. By using saturation limits, the objective function with the highest saturation limit can overpower the one with the lower limit. For example, a user may desire that an arm-to-patient collision avoidance must always override arm-to-arm collision avoidance functions for clinical reasons. In such cases, the null-space manager would allow the arm-to-patient avoidance to win a tiebreaker, and in response, when in a direct conflict, the manipulator would drive itself into a neighboring manipulator before penetrating the patient's body surface.

FIG. 14B is a schematic of the null-space coefficients in the null-space illustrating the saturation attribute described above. While original unsaturated vectors $\alpha_{1u}$ and $\alpha_{2u}$ may start out being equal and opposite, their saturation limits may be different, such that after saturation, $\alpha_1$ is shorter than $\alpha_2$. In this example, when multiple coefficients are summed together to arrive at a combined output, their saturation levels allows $\alpha_2$ to overpowers $\alpha_1$. Thus, if it is desired that a secondary objective, such as manipulator-to-manipulator collision avoidance, should not cancel a primary objective, such as patient-to-manipulator collision avoidance, appropriate saturation levels can be applied when combining objectives so that the primary objective overpowers any secondary objectives that conflict with or cancel the primary objective.

(c) Priority: This approach utilizes a continuous space mathematical concept, rather than a logical or discrete branching concept. For example, suppose one requirement is to allow a certain objective function to have unrestricted use of the null-space and that other objective functions are also to use the null-space, but without interfering with the former objective's usage. The concept of priority may be applied in such an example to allow the former objective access to the entire null-space, but only allows the latter objective access to the remaining unused orthogonal portion of the null-space. This approach is advantageous as the latter objective does not impede the former's usage, provided that the former's objective is linear in nature and orthogonal disturbances in the null-space have no effect on it. This approach may be performed as shown in the example of FIG. 14C. In this example, the objective functions operating at the highest priority may combine their outputs, such as by using one or both of the weighting and saturation techniques of (a) and (b) above. The resulting output vector is then mapped into the null-space. If the null-space has a dimension larger than 1, then the subspace of the null-space which is orthogonal to this output vector in the highest priority is then available to the next highest priority. The saturated weighted sum of all objective functions at the next highest priority are then projected onto the remaining null-space subspace. This process may continue until either all objective function priority levels have been addressed or until all null-space dimensions have been consumed. In another aspect, this approach may also be used to enable joint locking, or joint motion cancellation.

FIG. 14C shows a schematic of the coefficients vectors in the null-space illustrating the priority attribute described above. Here, the unmodified $\alpha_{p1o}$ has the highest priority, and therefore has unobstructed access to the entire null-space. In this example, the post-modification form, $\alpha_{p1}$ is identical to $\alpha_{p1o}$, while $\alpha_{p2o}$ is at a lower priority. Therefore, $\alpha_{p2o}$ only has access to the portion of the null-space not used by the higher priority $\alpha_{p1}$ (e.g., the portion that is orthogonal to $\alpha_{p1}$). This is obtained by projecting $\alpha_{p2o}$ onto that portion to obtain $\alpha_{p2}$ so as to allow the lower priority objective to be performed only to the extent that it does not interfere with the highest priority.

(d) Flag for master velocity limiting: Various null-space objective functions may be configured to be partially autonomous. For efficiency and usability reasons, it is useful in various applications to allow some autonomous functionality. However for safety reasons, it may be desired to allow the surgeon the ability to supervise and override autonomous motions. One way to allow this capability is to limit the magnitude of the outputs of certain null-space objective functions to be proportional to the master velocity. In this way, if the autonomous motion is undesirable, the surgeon can simply stop moving the masters, and the autonomous motion stops. However, at least some objective functions may not function correctly if master velocity limiting is applied to them. Therefore, this attribute tells the null-space manager whether or not to apply the master velocity limiting may be applied to a given objective function. Thus, certain objectives may be flagged in the null-space manager so that master velocity limiting is applied only to those objectives for which limiting is suitable.

(e) Flag for a saturated limited integrator (SLI) algorithm: The saturated limited integrator algorithm integrates commanded joint velocities into commanded joint positions, without violating either joint velocity limits or joint position limits (e.g. hard-stops). Some changes, such as those described below, may be made to certain embodiments in order to allow for two or more specific null-space behaviors. This attribute allows the manager to collate the consolidated null-space outputs from the multiple objective functions into two or more buckets, each associated with each of the two or more behaviors, such as in the following examples.

Behavior 1: The SLI algorithm has the authority to modify input joint velocity commands in order to fit the motion profile within the joint velocity and joint position limits. However, in order for null-space velocity commands to remain in the null-space, the SLI algorithm must limit only the velocity magnitudes but not directions. For example, to avoid disturbing the tool tip pose, the velocity vector may not include a direction change. This behavior may be useful for certain null-space objective outputs more than others and may be used selectively according to the null-space objectives of which consolidation is desired. Aspects of behavior 1 are depicted in FIG. 14D.

Behavior 2: One drawback associated with Behavior 1 is that it can lead to a phenomena often referred to as "sticky walls" (see FIG. 14D), which may occur, for example, when the manipulator is against a joint limit wall and is commanded to slide along the wall. For such a move, applying Behavior 1, would not change the direction and would only shorten the length to 0 for any sliding command, (e.g., any move which has a component toward the wall). Therefore, no sliding would be permitted, and the joint limits would behave like sticky walls. Certain algorithms may circumvent this issue by performing velocity limiting on a DOF-by-DOF basis. In such a case, only the DOF associated with the joint limit would be set to zero, while the remaining DOFs would be unaffected. The result would be a sliding command along the joint limit, which is the desired behavior when commanding tool tip motion. In certain embodiments, the joint velocity limiting may be applied in a vectorized manner, while the joint position limiting is applied in a DOF-by-DOF fashion.

Figure 14D:
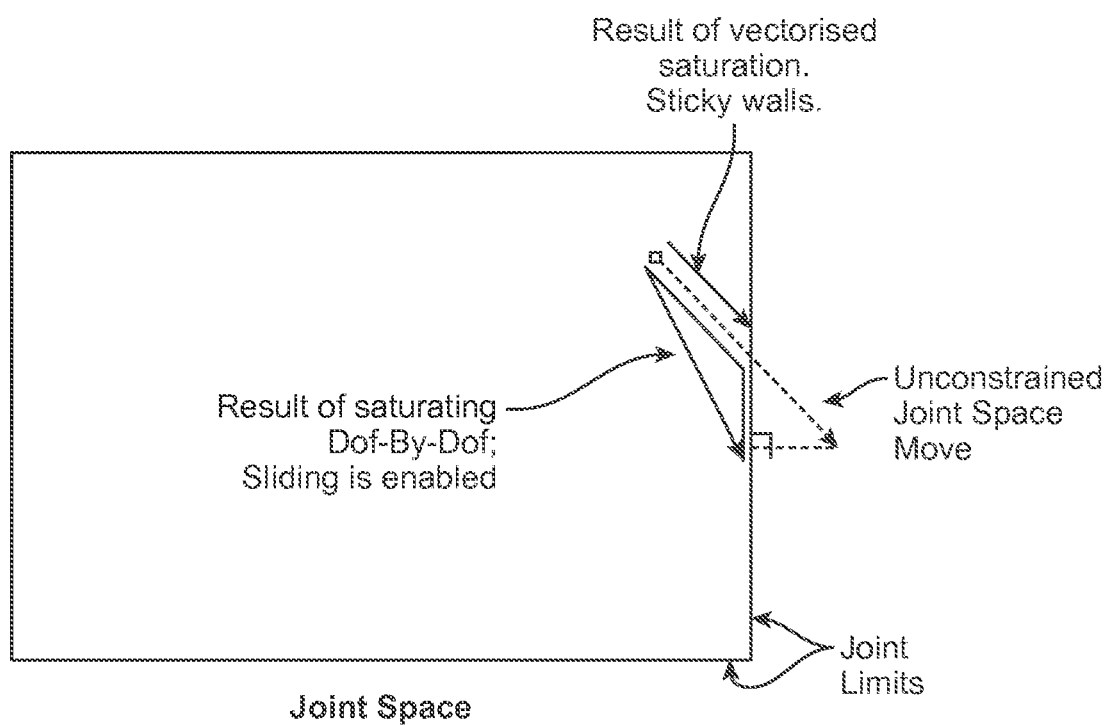

FIG. 14D shows a schematic of the joint space with its limits (e.g., hard-stops drawn by borders) illustrating the SLI concepts described above. The dashed arrow in the upper right shows the unsaturated arrow, which penetrates the joint limits, and must therefore be saturated. The shorter arrow above it illustrates Behavior 1, (e.g. only a magnitude change with no direction change). In this case, no sliding would occur. The triangle below the dashed arrow shows Behavior 2. In this case, only the component of the unsaturated (dashed) arrow pointing toward the wall (horizontal) is saturated, while the vertical component is left as is. The result allows sliding along the joint limit wall. Since this corresponds to a direction change, and therefore may not appropriate for various null-space moves.

(f) Other attributes: Other attributes in accordance with these general concepts, but which are not currently used or that may be imagined by one of skill in the art could be used to treat multiple objective functions differently in a specific way, through the null-space manager. In addition, it is understood that various combinations of the above attributes may be used and applied in a variety of ways based on the desired objectives and/or the associated null-space movements.

Figure 15:
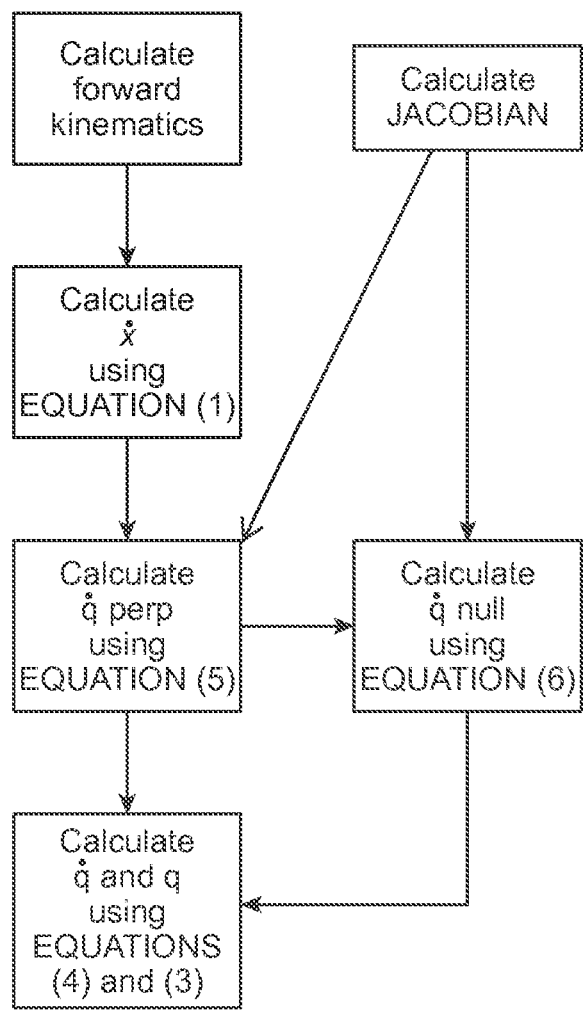
FIG. 15 illustrate a block diagram used to implement general algorithms in an example manipulator assembly.

FIG. 15 shows a simplified schematic of the required blocks needed to implement the general algorithms to control the patient side cart joint states, in relation to the equations discussed above. According to the method of FIG. 15, the system calculates the forward kinematics of the manipulator arm, then calculates dx/dt using Equation (1), calculates $dq_{perp}/dt$ using Equation (5), and then calculates $dq_{null}/dt$ from z which may depend on $dq_{perp}/dt$ and the Jacobian using Equation (6). From the calculated $dq_{perp}/dt$ and $dq_{null}/dt$ the system then calculates dq/dt and q using Equations (4) and (3), respectively, thereby providing the calculated movement by which the controller can effect the desired reconfiguration of the manipulator while maintaining the desired state of the end effector (and/or location of the remote center).

Figure 16:
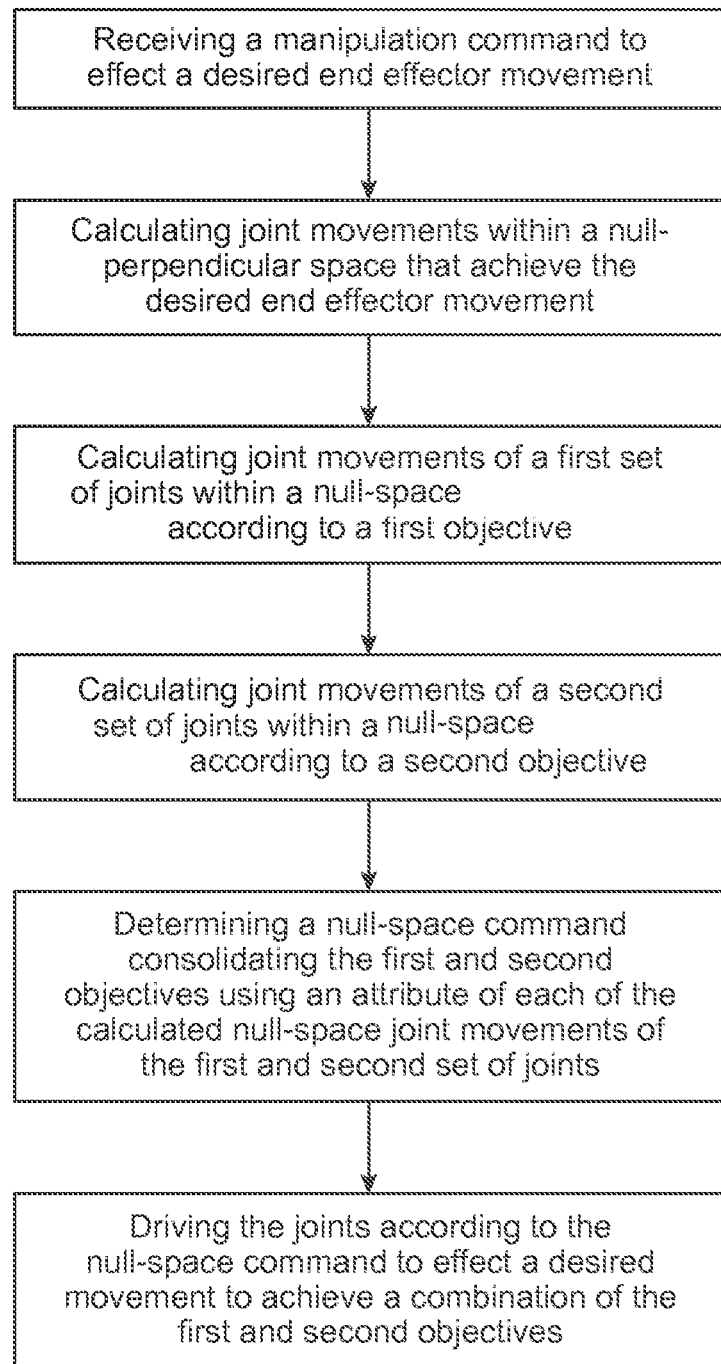
FIGS. 16-17 illustrate block diagrams of example methods in accordance with the present invention.
Figure 17:
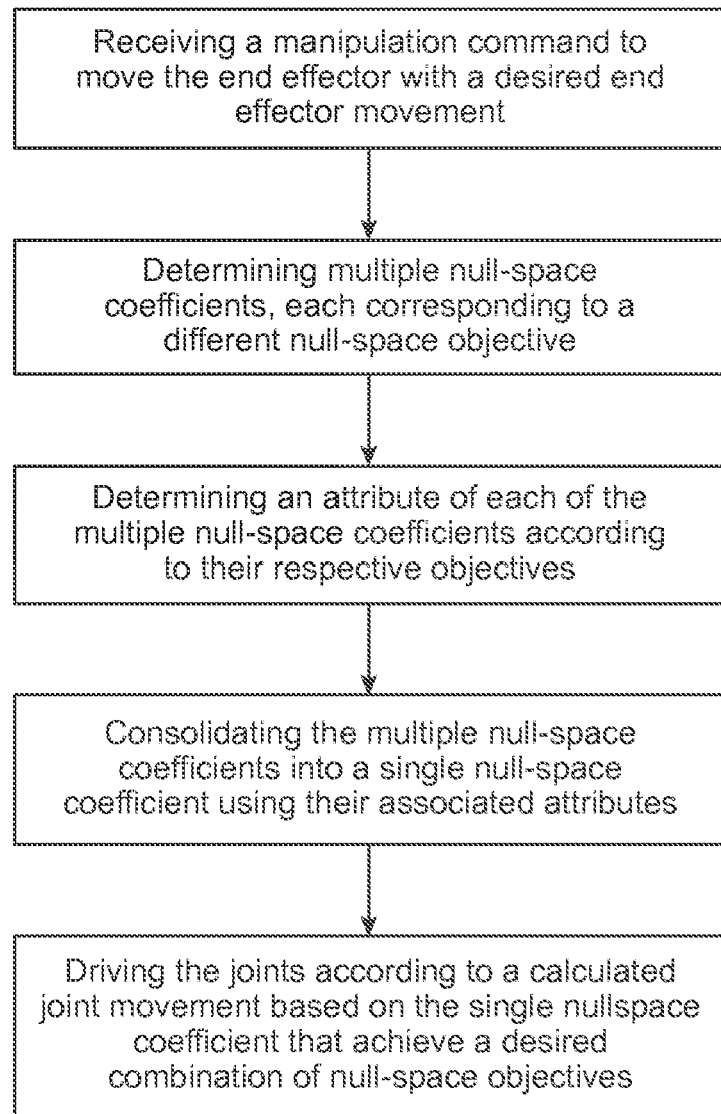

FIGS. 16-17 show flow charts of example methods in accordance with aspects of the present invention. As shown in FIG. 16, an example method performed by the manipulator may system include: receiving a manipulation command to effect a desired end effector movement; calculating joint movement of a first set of joints for a first objective; calculating joint movements of a second set of joints within a null-space according to a second objective; determining a null-space command consolidating the first and second objectives using an attribute of each of the calculated null-space joint movements of the first and second set of joints; and driving the joints according to the null-space command to effect a desired movement to achieve a combination of the first and second objectives. As shown in FIG. 17, an example method of the manipulator system may include: receiving a manipulation command to move the end effector with a desired end effector movement; determining multiple null-space coefficients, each corresponding to a different null-space objective; determining an attribute of each of the multiple null-space coefficients according to their respective objectives; consolidating the multiple null-space coefficients into a single null-space coefficient using their associated attributes; and driving the joints according to a calculated joint movement based on the single null-space coefficient to achieve a desired combination of null-space objectives.

While the example embodiments have been described in some detail for clarity of understanding and by way of example, a variety of adaptations, modifications, and changes will be obvious to those of skill in the art. Hence, the scope of the present invention is limited solely by the appended claims.

What is claimed is:

1. A method, implemented at a processor, for moving a manipulator arm, the manipulator arm including a movable distal portion, a proximal portion coupled to a base, and a plurality of joints between the distal portion and the base, the plurality of joints having sufficient degrees of freedom to allow a range of differing joint states of the plurality of joints for a given state of the distal portion, the method comprising:

the processor calculating a first movement of the plurality of joints in accordance with a first objective of a plurality of objectives, the plurality of objectives being for motions in a null-space of a Jacobian of the manipulator arm, wherein the first movement is in the null-space;

the processor calculating a second movement of the plurality of joints in accordance with a second objective of the plurality of objectives, wherein the second movement is in the null-space;

the processor determining a combined movement of the plurality of joints by using a combining behavior selected from the group consisting of:
combining the first and second movements while limiting an overall magnitude of the combined movement without changing a direction of the combined movement, and
combining the first and second movements while limiting a magnitude of the combined movement degree-of-freedom by degree-of-freedom; and the processor driving the plurality of joints to effect the combined movement of the plurality of joints.

2. The method of claim 1, wherein the combining behavior consists of: the processor combining the first and second movements while limiting an overall magnitude of the combined movement without changing a direction of the combined movement.

3. The method of claim 1, wherein the combining behavior consists of: combining the first and second movements while limiting a magnitude of the combined movement degree-of-freedom by degree-of-freedom.

4. The method of claim 1, wherein the first objective is associated with a first attribute indicating whether the first movement is to be limited in overall magnitude or degree-of-freedom by degree-of-freedom, and the second objective is associated with a second attribute indicating whether the second movement is to be limited in overall magnitude or degree-of-freedom by degree-of-freedom, and wherein the processor determining the combined movement further comprises:
determining, based on the first and second attributes, whether to limit the overall magnitude of the combined movement, or to limit the magnitude of the combined movement degree-of-freedom by degree-of-freedom.

5. The method of claim 1, wherein the processor determining the combined movement further comprises:
the processor limiting at least one movement in relation to a master velocity, wherein the master velocity is associated with a commanded movement to move the distal portion, and wherein the at least one movement is selected from a group consisting of: the first movement, the second movement, and the combined movement.

6. A system comprising:
a manipulator arm including a movable distal portion, a proximal portion coupled to a base, and a plurality of joints between the distal portion and the base, the plurality of joints having sufficient degrees of freedom to allow a range of differing joint states of the plurality of joints for a given state of the distal portion;
a processor coupled to the manipulator arm, the processor being configured to perform operations including:
calculating a first movement of the plurality of joints in accordance with a first objective of a plurality of objectives, the plurality of objectives being for motions in a null-space of a Jacobian of the manipulator arm, wherein the first movement is in the null-space;

calculating a second movement of the plurality of joints in accordance with a second objective of the plurality of objectives, wherein the second movement is in the null-space;

determining a combined movement of the plurality of joints by using a combining behavior selected from the group consisting of:

combining the first and second movements while limiting an overall magnitude of the combined movement without changing a direction of the combined movement, and combining the first and second movements while limiting a magnitude of the combined movement degree-of-freedom by degree-of-freedom; and driving the plurality of joints to effect the combined movement of the plurality of joints.

7. The system of claim 6, wherein the combined movement is determined to not violate a joint velocity limit or a joint position limit.

8. The system of claim 6, wherein the combining behavior consists of: combining the first and second movements while limiting an overall magnitude of the combined movement without changing a direction of the combined movement.

9. The system of claim 8, wherein the limiting the overall magnitude of the combined movement without changing the direction of the combined movement avoids disturbing a tool tip pose of a tool supported by the manipulator arm.

10. The system of claim 6, wherein the combining behavior consists of: combining the first and second movements while limiting a magnitude of the combined movement degree-of-freedom by degree-of-freedom.

11. The system of claim 6, wherein the first objective is associated with a first attribute indicating whether the first movement is to be limited in overall magnitude or degree-of-freedom by degree-of-freedom, and the second objective is associated with a second attributed indicating whether the second movement is to be limited in overall magnitude or degree-of-freedom by degree-of-freedom, and wherein the processor determining the combined movement further comprises:

determining, based on the first and second attributes, whether to limit the overall magnitude of the combined movement, or to limit the magnitude of the combined movement degree-of-freedom by degree-of-freedom.

12. The system of claim 6, wherein the determining the combined movement further comprises:

the processor limiting at least one movement in relation to a master velocity, wherein the master velocity is associated with a commanded movement to move the distal portion, and wherein the at least one movement is selected from a group consisting of: the first movement, the second movement, and the combined movement.

13. The system of claim 12, wherein the limiting the at least one movement in relation to the master velocity comprises:

determining whether to limit the first movement in relation to the master velocity based on the first objective; and determining whether to limit the second movement in relation to the master velocity based on the second objective.

14. The system of claim 12, wherein the limiting the at least one movement in relation to the master velocity results in no motion of the plurality of joints when a master control input device providing the master velocity is not moving.

15. The system of claim 6, wherein the first objective is associated with a first attribute, and the second objective is associated with a second attribute, and wherein the determining the combined movement further comprises:

combining the first and second movements using the first and second attributes.

16. The system of claim 15:

wherein the first attribute comprises a first weight for the first objective, the second attribute comprises to a second weight for the second objective, and combining the first and second movements using the first and second attributes comprises: using the first and second weights to calculate a weighted combination of the first and second movements; or wherein the first attribute comprises a saturation value, and combining the first and second movements using the first and second attributes comprises: applying the saturation value to limit the first movement.

17. The system of claim 15, wherein the first attribute comprises a first priority for the first objective, and the second attribute comprises a second priority for the second objective; and combining the first and second movements using the first and second attributes comprises:

in response to the first priority being higher than the second priority, providing the first movement with higher priority access than the second movement to the null-space; and in response to the second priority being higher than the first priority, providing the second movement with higher priority access than the first movement to the null-space.

18. The system of claim 6, the operations further including:

receiving a manipulation command to move the distal portion;

calculating a distal-portion movement of the plurality of joints to move the distal portion;

driving the plurality of joints to effect the distal-portion movement of the plurality of joints in combination with the combined movement of the plurality of joints.

19. A non-transitory computer-readable medium storing instructions that, when executed by a processor, cause the processor to perform operations for moving a manipulator arm, the manipulator arm including a movable distal portion, a proximal portion coupled to a base, and a plurality of joints between the distal portion and the base, the plurality of joints having sufficient degrees of freedom to allow a range of differing joint states of the plurality of joints for a given state of the distal portion, the operations comprising:

calculating a first movement of the plurality of joints in accordance with a first objective of a plurality of objectives, the plurality of objectives being for motions in a null-space of a Jacobian of the manipulator arm, wherein the first movement is in the null-space;

calculating a second movement of the plurality of joints in accordance with a second objective of the plurality of objectives, wherein the second movement is in the null-space;

determining a combined movement of the plurality of joints by:

combining the first and second movements while limiting an overall magnitude of the combined movement without changing a direction of the combined movement, or combining the first and second movements while limiting a magnitude of the combined movement degree-of-freedom by degree-of-freedom; and driving the plurality of joints to effect the combined movement of the plurality of joints.

20. The non-transitory computer-readable medium of claim 19, wherein the determining the combined movement further comprises:
  limiting at least one movement in relation to a master velocity, wherein the master velocity is associated with a commanded movement to move the distal portion, and wherein the at least one movement is selected from a group consisting of: the first movement, the second movement, and the combined movement.

* * * * *